(12) United States Patent
Kline et al.

(10) Patent No.: US 9,375,362 B2
(45) Date of Patent: Jun. 28, 2016

(54) FASTENERS HAVING IMPROVED COMFORT

(71) Applicant: The Procter & Gamble Company, Cincinnati, OH (US)

(72) Inventors: Mark James Kline, Okeana, OH (US); Anna Elizabeth Macura, Loveland, OH (US); Michael Irwin Lawson, Fairfield, OH (US); Ronald Joseph Zink, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/973,787

(22) Filed: Dec. 18, 2015

(65) Prior Publication Data

US 2016/0100998 A1    Apr. 14, 2016

Related U.S. Application Data

(60) Continuation of application No. 12/946,121, filed on Nov. 15, 2010, now Pat. No. 9,241,847, which is a division of application No. 11/638,748, filed on Dec. 14, 2006, now Pat. No. 7,870,652.

(60) Provisional application No. 60/752,838, filed on Dec. 22, 2005.

(51) Int. Cl.
  *A61F 13/49*    (2006.01)
  *A61F 13/56*    (2006.01)
  (Continued)

(52) U.S. Cl.
  CPC ....... *A61F 13/49019* (2013.01); *A44B 18/0069* (2013.01); *A61F 13/49014* (2013.01);
  (Continued)

(58) Field of Classification Search
  CPC ........... A61F 13/49019; A61F 13/5655; A61F 13/5622; A61F 13/49014; A61F 13/62;
  A61F 2013/49041; A61F 2013/49057; A61F 2013/15357; A61F 13/58; A61F 13/622; Y10T 24/2783; Y10T 24/27; A44B 18/0069
  USPC ......... 24/306, 442–452; 428/100, 44; 525/64, 525/66, 166, 179; 604/391, 386
  See application file for complete search history.

(56) References Cited

U.S. PATENT DOCUMENTS

| | | | |
|---|---|---|---|
| 3,860,003 | A | 1/1975 | Buell |
| 3,911,173 | A | 10/1975 | Sprague, Jr. |

(Continued)

FOREIGN PATENT DOCUMENTS

| | | |
|---|---|---|
| EP | 318087 | 12/1991 |
| EP | 0880956 | 12/1998 |

(Continued)

OTHER PUBLICATIONS

PCT International Search Report, PCT/IB2006/054947, mailed May 30, 2007, 11 pages.

(Continued)

*Primary Examiner* — Robert J Sandy
*Assistant Examiner* — Rowland Do
(74) *Attorney, Agent, or Firm* — Christian M. Best

(57) ABSTRACT

A fastening member has inboard and outboard ends, a panel region, an end region, and a stiffening element. The panel region is disposed adjacent to the inboard end and has first and second layers. The first and second layers are joined in a face-to-face orientation. The end region is disposed adjacent to the outboard end and has a fastening element zone and an intermediate zone. The intermediate zone is disposed between the fastening element zone and the panel region adjacent an interface between the panel and end regions. The stiffening element is disposed in the end region and has a stiffness of greater than about 200 N/m. A portion of the stiffening element is disposed between the first layer and the second layer and is joined to the first layer and the second layer. The portion is disposed adjacent to the interface between the panel region and the end region.

30 Claims, 10 Drawing Sheets

(51) Int. Cl.
*A44B 18/00* (2006.01)
*A61F 13/58* (2006.01)
*A61F 13/62* (2006.01)
*A61F 13/15* (2006.01)

(52) U.S. Cl.
CPC ......... *A61F13/5622* (2013.01); *A61F 13/5655* (2013.01); *A61F 13/58* (2013.01); *A61F 13/62* (2013.01); *A61F 13/622* (2013.01); *A61F 2013/15357* (2013.01); *A61F 2013/49041* (2013.01); *A61F 2013/49057* (2013.01); *Y10T 24/27* (2015.01); *Y10T 24/2783* (2015.01)

(56) References Cited

U.S. PATENT DOCUMENTS

| | | |
|---|---|---|
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,673,402 A | 6/1987 | Weisman et al. |
| 4,695,278 A | 9/1987 | Lawson |
| 4,785,996 A | 11/1988 | Ziecker et al. |
| 4,815,172 A * | 3/1989 | Ward .................... A44B 18/00 24/16 R |
| 4,834,735 A | 5/1989 | Alemany et al. |
| 4,842,666 A | 6/1989 | Werenicz |
| 4,846,815 A | 7/1989 | Scripps |
| 4,869,724 A * | 9/1989 | Scripps ................ A61F 13/581 604/389 |
| 4,888,231 A | 12/1989 | Angstadt |
| 4,892,536 A | 1/1990 | DesMarais et al. |
| 4,909,803 A | 3/1990 | Aziz et al. |
| 4,916,005 A | 4/1990 | Lippert et al. |
| 4,940,464 A | 7/1990 | Van Gompel et al. |
| 4,963,140 A * | 10/1990 | Robertson ............. A61F 13/581 604/389 |
| 4,968,312 A | 11/1990 | Khan |
| 4,990,147 A | 2/1991 | Freeland |
| 5,006,394 A | 4/1991 | Baird |
| 5,019,073 A | 5/1991 | Roessler et al. |
| 5,037,416 A | 8/1991 | Allen et al. |
| 5,062,840 A | 11/1991 | Holt et al. |
| 5,092,861 A | 3/1992 | Nomura et al. |
| 5,137,537 A | 8/1992 | Herron et al. |
| 5,147,345 A | 9/1992 | Young et al. |
| 5,151,092 A | 9/1992 | Buell et al. |
| 5,171,236 A | 12/1992 | Dreier et al. |
| 5,176,671 A | 1/1993 | Roessler et al. |
| 5,221,274 A | 6/1993 | Buell et al. |
| 5,246,433 A | 9/1993 | Hasse et al. |
| 5,260,345 A | 11/1993 | DesMarais et al. |
| 5,269,775 A | 12/1993 | Freeland et al. |
| 5,306,266 A | 4/1994 | Freeland |
| 5,312,387 A | 5/1994 | Rossini et al. |
| 5,318,555 A | 6/1994 | Siebers et al. |
| 5,342,338 A | 8/1994 | Roe |
| 5,380,313 A | 1/1995 | Goulait et al. |
| 5,383,872 A | 1/1995 | Roessler et al. |
| 5,387,207 A | 2/1995 | Dyer et al. |
| 5,397,318 A | 3/1995 | Dreier |
| 5,399,219 A | 3/1995 | Roessler et al. |
| 5,407,439 A | 4/1995 | Goulait |
| 5,460,622 A | 10/1995 | Dragoo et al. |
| 5,496,298 A | 3/1996 | Kuepper et al. |
| 5,514,121 A | 5/1996 | Roe et al. |
| 5,518,801 A | 5/1996 | Chappell et al. |
| 5,540,671 A | 7/1996 | Dreier |
| 5,540,673 A | 7/1996 | Thomas et al. |
| 5,542,942 A | 8/1996 | Kline et al. |
| 5,549,591 A | 8/1996 | Landvogt |
| 5,549,592 A | 8/1996 | Fries et al. |
| 5,554,142 A | 9/1996 | Dreier et al. |
| 5,569,233 A | 10/1996 | Goulait |
| 5,569,234 A | 10/1996 | Buell et al. |
| 5,571,096 A | 11/1996 | Dobrin et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,653,703 A | 8/1997 | Roe et al. |
| 5,669,900 A | 9/1997 | Bullwinkel et al. |
| 5,672,404 A | 9/1997 | Callahan et al. |
| 5,685,873 A | 11/1997 | Bruemmer |
| H1732 H | 6/1998 | Johnson |
| 5,759,317 A | 6/1998 | Justmann |
| 5,865,823 A | 2/1999 | Curro |
| 5,897,545 A | 4/1999 | Kline et al. |
| 5,900,101 A | 5/1999 | Justmann |
| 5,904,675 A | 5/1999 | Laux et al. |
| 5,938,648 A | 8/1999 | LaVon et al. |
| 5,941,864 A | 8/1999 | Roe |
| 5,957,908 A | 9/1999 | Kline et al. |
| 5,968,025 A | 10/1999 | Roe et al. |
| 5,977,430 A | 11/1999 | Roe et al. |
| 5,993,433 A | 11/1999 | St. Louis et al. |
| 5,997,520 A | 12/1999 | Ahr et al. |
| 6,007,527 A * | 12/1999 | Kawaguchi ......... A61F 13/5512 156/315 |
| 6,010,490 A | 1/2000 | Freeland et al. |
| 6,013,063 A | 1/2000 | Roe et al. |
| 6,120,487 A | 9/2000 | Ashton |
| 6,120,489 A | 9/2000 | Johnson et al. |
| 6,156,424 A | 12/2000 | Taylor |
| 6,168,584 B1 | 1/2001 | Allen et al. |
| 6,225,236 B1 | 5/2001 | Nishimoto et al. |
| 6,235,137 B1 | 5/2001 | Van Eperen et al. |
| 6,248,097 B1 | 6/2001 | Beitz et al. |
| 6,454,753 B1 | 9/2002 | Shimoe et al. |
| 6,623,469 B1 | 9/2003 | Thomas |
| 6,652,693 B2 | 11/2003 | Burriss et al. |
| 6,680,422 B2 | 1/2004 | Roe |
| 6,716,441 B1 | 4/2004 | Osborne et al. |
| 6,730,069 B2 | 5/2004 | Tanzer et al. |
| 7,195,729 B2 | 3/2007 | Jackson et al. |
| 7,198,622 B2 | 4/2007 | Dahlgren |
| 7,388,511 B2 | 6/2008 | Amand |
| 7,870,652 B2 | 1/2011 | Kline et al. |
| 8,161,573 B1 * | 4/2012 | Burns-Cox ......... A41D 13/1245 2/227 |
| 8,382,736 B2 | 2/2013 | Kline et al. |
| 9,241,847 B2 | 1/2016 | Kline et al. |
| 9,241,848 B2 | 1/2016 | Kline et al. |
| 2001/0053905 A1 | 12/2001 | Shingu et al. |
| 2003/0009144 A1 | 1/2003 | Tanzer et al. |
| 2003/0077430 A1 | 4/2003 | Grimm et al. |
| 2003/0088220 A1 | 5/2003 | Molander et al. |
| 2003/0100879 A1 | 5/2003 | Kline et al. |
| 2003/0109844 A1 | 6/2003 | Gibbs |
| 2003/0233082 A1 | 12/2003 | Kline et al. |
| 2004/0063369 A1 | 4/2004 | Ahn et al. |
| 2004/0116888 A1 | 6/2004 | Dorschner |
| 2004/0122413 A1 | 6/2004 | Roessler et al. |
| 2004/0181200 A1 | 9/2004 | Desai et al. |
| 2004/0193133 A1 | 9/2004 | Desai et al. |
| 2005/0004547 A1 | 1/2005 | Lavash |
| 2005/0015938 A1 | 1/2005 | Shepard et al. |
| 2005/0027267 A1 | 2/2005 | Van Dyke et al. |
| 2005/0249915 A1 | 11/2005 | Wood et al. |
| 2006/0292328 A1 | 12/2006 | Baldauf et al. |
| 2007/0130732 A1 | 6/2007 | Matsumura et al. |
| 2007/0143972 A1 | 6/2007 | Kline et al. |
| 2008/0021432 A1 | 1/2008 | Kline et al. |
| 2011/0040274 A1 | 2/2011 | Kline et al. |

(56) References Cited

U.S. PATENT DOCUMENTS

| | | | |
|---|---|---|---|
| 2011/0082436 A1* | 4/2011 | Meetz | A61F 13/5512 604/386 |
| 2013/0133163 A1 | 5/2013 | Kline et al. | |
| 2014/0228799 A1 | 8/2014 | Kline et al. | |

FOREIGN PATENT DOCUMENTS

| | | |
|---|---|---|
| EP | 0734243 B1 | 6/2000 |
| JP | 10155834 | 12/1996 |
| JP | 2000014702 A | 1/2000 |
| JP | 2001145663 | 5/2001 |
| JP | 2005245555 A | 9/2005 |
| WO | WO9414395 | 7/1994 |
| WO | WO-95/16746 A1 | 6/1995 |
| WO | WO9524173 | 9/1995 |
| WO | WO9604873 | 2/1996 |
| WO | WO03082167 | 10/2003 |
| WO | WO2004030763 | 4/2004 |
| WO | WO2004082918 | 9/2004 |
| WO | WO2005110731 | 11/2005 |

OTHER PUBLICATIONS

All Office Actions, Responses and Claims, U.S. Appl. No. 14/967,636.
All Office Actions, Responses and Claims, U.S. Appl. No. 14/257,026.
All Office Actions, Responses and Claims, U.S. Appl. No. 13/746,378.
All Office Actions, Responses and Claims, U.S. Appl. No. 12/913,932.
All Office Actions, Responses and Claims, U.S. Appl. No. 11/895,169.
All Office Actions, Responses and Claims, U.S. Appl. No. 11/638,988.
All Office Actions, Responses and Claims, U.S. Appl. No. 11/638,748.
All Office Actions, Responses and Claims, U.S. Appl. No. 12/946,121.
All Office Actions, Responses and Claims, U.S. Appl. No. 12/946,140.

* cited by examiner

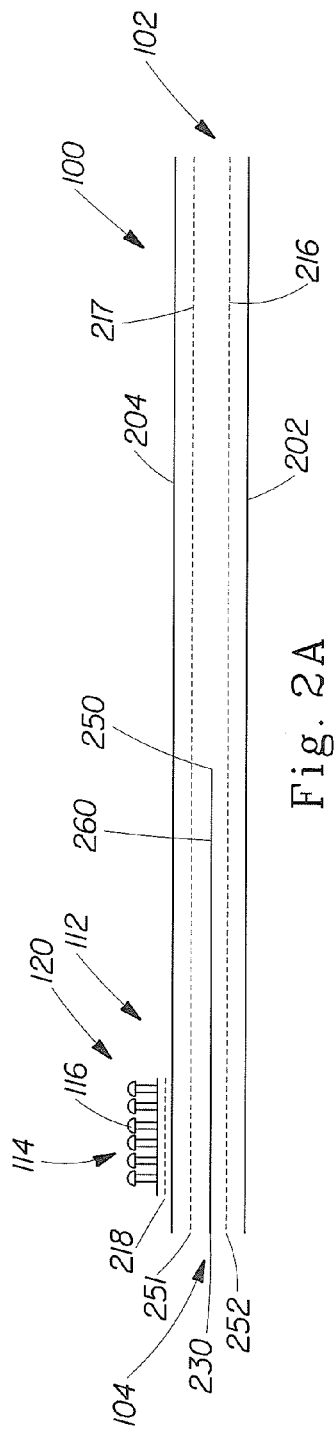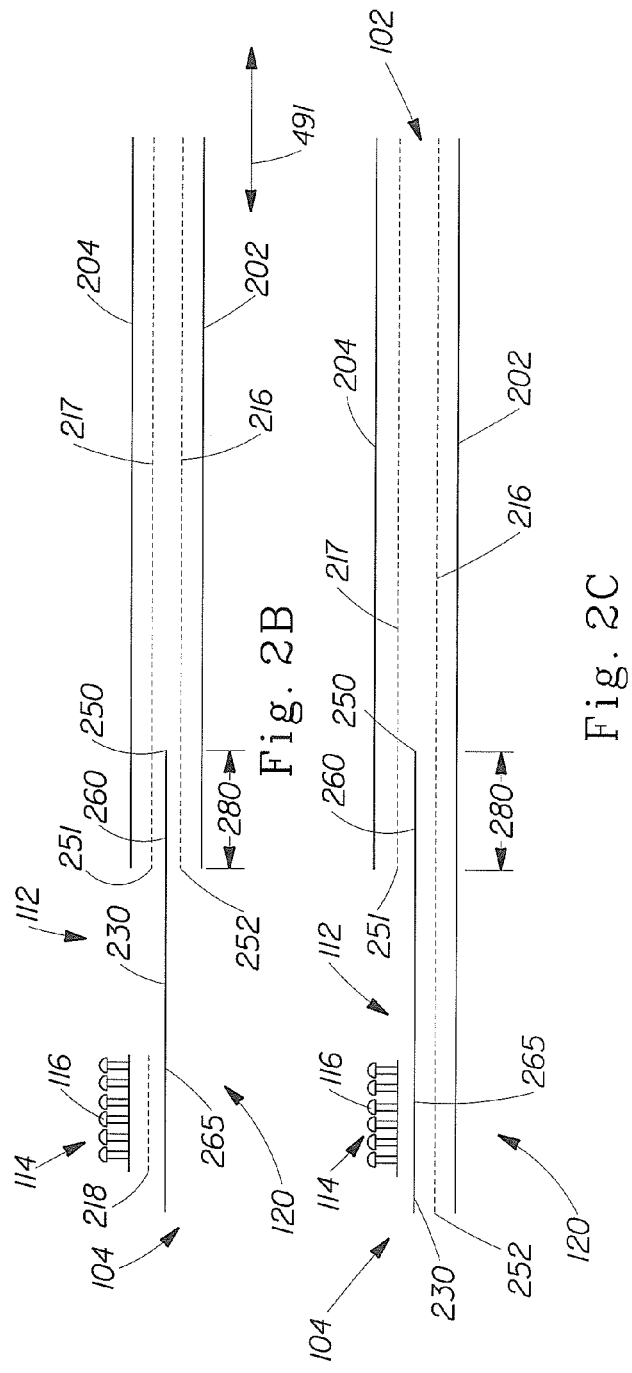

FASTENERS HAVING IMPROVED COMFORT

CROSS REFERENCES TO RELATED APPLICATIONS

This application is a continuation of U.S. patent application Ser. No. 12/946,121, filed on Nov. 15, 2010, which is a divisional of U.S. patent application Ser. No. 11/638,748, filed on Dec. 14, 2006, now U.S. Pat. No. 7,870,652, granted on Jan. 18, 2011, which claims the benefit of U.S. Provisional Patent Application No. 60/752,838, filed on Dec. 22, 2005, the entire disclosures of each are hereby incorporated by reference.

FIELD OF THE INVENTION

The present invention relates to fastening members. Particularly, the present invention relates to fastening members having surface fastening elements and having a portion which has increased resistance to buckling under applied load.

BACKGROUND OF THE INVENTION

Refastenable mechanical fastening systems can be used in a wide number of applications. For example, such refastenable fastening systems can be used to connect one portion of a disposable absorbent article to another portion of the disposable absorbent article.

In general, mechanical fastening systems may comprise a fastening member having a receiving/female component and/or a fastening member having an engaging/male component. In some mechanical fastening systems, the engaging member comprises a plurality of hook elements, and the receiving component comprises a plurality of loop elements. In a fastened state, the hook elements are typically entangled with the loop elements such that a connection between the engaging and receiving components is formed.

During fastening, a tension can be applied to the fastening member. The applied tension can induce compressive forces in the fastening member which can cause a portion of the fastening member to contract (neck). Additionally, the compressive forces can often act on the engaging component and cause the engaging component to buckle.

Unfortunately, when buckled, the hook elements of the engaging component can be out of alignment, e.g. not in the same plane. This misalignment of hook elements can cause less than 100% of the hook elements to engage with the receiving component thereby reducing the performance of the fastening system.

Typically, a stiffener can be added to the fastening member to provide added resistance to buckling. However, if the stiffener is not adequately secured, edges of the stiffener can become exposed when the portion of the fastening member necks. The exposed edges can, in some cases cause irritation to skin of a wearer.

Consequently, a need exists for a fastening member which can provide increased resistance to buckling and reduce the likelihood of exposed edges of a stiffening material.

SUMMARY OF THE INVENTION

A fastening member constructed in accordance with the present invention can provide improved fastening system performance. In some embodiments, a fastening member has an inboard end and an outboard end. The fastening member further comprises a panel region, an end region, and a stiffening element. The panel region is disposed adjacent to the inboard end and comprises a first layer and a second layer joined to the first layer in a face-to-face orientation.

The end region is disposed adjacent to the outboard end, and the end region comprises a fastening element zone and an intermediate zone. The intermediate zone is disposed between the fastening element zone and the panel region adjacent an interface between the panel region and the end region.

The stiffening element disposed in the end region and has a stiffness of greater than about 200 N/m. The stiffening element is disposed between the first layer and the second layer and is joined to the first layer and the second layer proximate to the interface between the panel region and the end region.

In other embodiments, the fastening member may further comprise an elastomeric element disposed between the first layer and the second layer such that the elastomeric element is sandwiched between the first layer and the second layer. Additionally, the fastening element zone can have a first stiffness and the intermediate zone can have a second stiffness, wherein the first stiffness is greater than the first stiffness. The fastening member may further comprise a fastening element disposed in the end region which defines the fastening element zone.

BRIEF DESCRIPTION OF THE DRAWINGS

FIG. 2A is a cross sectional view showing the fastening member of FIG. 1A as seen through line 2A-2A.

FIGS. 2B-2C are cross sectional views showing other embodiments of the fastening member of FIG. 1A.

DETAILED DESCRIPTION OF THE INVENTION

Figure 1A:
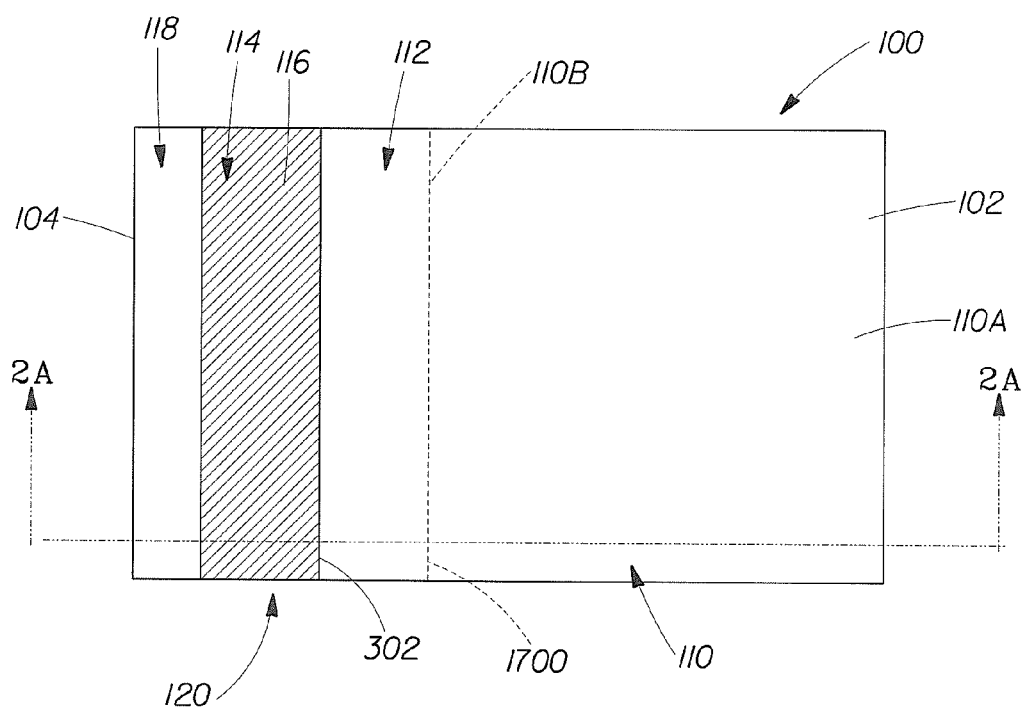
FIG. 1A is a plan view showing a fastening member constructed in accordance with the present invention.

Definitions:

As used herein, the terms "absorbent article" and "article" refer to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than ten uses, preferably after no more than five uses, and most preferably after a single use (although certain components may be recycled, reused, or composted).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein "elastically extensible" refers to characteristics of extensible materials that have the ability to return to approximately their original dimensions after a force that extended the extensible material is removed.

The terms "exterior surface" and "interior surface" as used herein refer to relative locations on a portion of a fastening member as shown. The terms "exterior surface" and "interior surface" are not necessarily indicative of locations with respect to the fastening member after the fastening member has been joined to an article.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "longitudinal" is used herein to refer to a direction which is generally parallel to the longest edge of an element except where otherwise noted. In the context of disposable absorbent articles, a "longitudinal" direction "runs substantially perpendicular from a waist edge to an opposing waist edge of the article and generally parallel to the maximum linear dimension of the article. Directions within ±45 degrees of the longitudinal direction are considered to be "longitudinal".

The term "lateral" refers to a direction running generally perpendicular to and in the same plane as the "longitudinal" direction. In the context of disposable absorbent articles, a "lateral" direction runs from one longitudinal edge of the article to an opposing longitudinal edge of the article. Directions within ±45° of the lateral direction are considered to be "lateral".

The terms "machine direction" or "MD" refer to a direction which is generally parallel to the forward direction of a material, member, element, item, etc. through a process. For example, nonwovens are typically formed with a machine direction that corresponds to the long or rolled direction of fabrication. The machine direction can also be the primary direction of fiber orientation in the nonwoven.

The terms "cross direction" or "CD" refer to a direction which is generally perpendicular to and in the same plane as the machine direction.

The terms "pant", "training pant", "closed diaper", "prefastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

Description:

The fastening member of the present invention may provide improved fastening capability. The fastening member of the present invention may be incorporated into a variety of consumer and commercial goods that may benefit from having a fastening member constructed in accordance with the present invention. In any of the embodiments described herein, the fastening member may be a separate element added to the commercial good. For example, the fastening member may be a discrete structure joined to any component (e.g., a topsheet, an absorbent core, a backsheet, a fastening system, a cuff, etc.) of an absorbent article or other commercial good (e.g., a wrap, a medical product, etc.). Alternatively, the fastening member may be constructed as part or all of any element of the commercial good or fastener. For example, the fastening member may be constructed as part or all of any component (e.g., a topsheet, an absorbent core, a backsheet, a fastening system, a cuff, etc.) of an absorbent article or other commercial good (e.g., a wrap, a medical product, etc.). Further, the fastening member may be disposed in any suitable location on or in the commercial good or fastener. For example, the fastening member may be disposed on a garment-facing surface of, body-facing surface of, or contained within the commercial good or fastener.

As shown in FIG. 1A, a fastening member 100 constructed in accordance with the present invention may comprise an inboard end 102 and an outboard end 104. The fastening member 100 may further comprise a panel region 110, an end region 120, and a stiffening element 230 (shown in FIG. 2A). The panel region 110 and the end region 120 are separated by an interface 1700 which comprises a distal end 110B of the panel region 110. The panel region 110 can be disposed adjacent to the inboard end 102 of the fastening member 100. The panel region 110 may further comprise a proximal edge 110A and the distal edge 110B. As shown, the proximal edge 110A can be disposed adjacent to the inboard end 102.

In some embodiments, the panel region 110 can be elastically extensible. In some embodiments, the panel region 110 may be extensible but not elastically extensible. For example, the panel region 110 may lack the ability to return to approximately its original dimensions after a force that extended the panel region is removed.

The panel region 110 can be more extensible than the end region 120. For example, in some embodiments, the panel region 110 can extend to greater than or equal to about 100% at an applied load of about 0.5 N/cm. In some embodiments, the panel region 110 can extend to greater than or equal to about 100% at an applied load of about 1.5 N/cm. In some embodiments, the panel region 110 can extend to greater than or equal to about 100% at an applied load of about 4.0 N/cm. In some embodiments, the panel region 110 can extend to greater than or equal to about 150% at an applied load of about 0.5 N/cm. In some embodiments, the panel region 110 can extend to greater than or equal to about 150% at an applied load of about 1.5 N/cm. In some embodiments, the panel region 110 can extend to greater than or equal to about 150% at an applied load of about 4.0 N/cm.

In contrast, the end region 120 can extend to less than about 100% at an applied load of about 4.0 N/cm, in some embodiments. In some embodiments, the end region 120 can extend to less than about 50% at the applied load mentioned above. In some embodiments, the end region 120 can extend to less than about 15% at the applied load mentioned above.

The end region 120 can be disposed adjacent to the outboard end 104 of the fastening member 100. The end region 120 may comprise a fastening element zone 114 and an intermediate zone 112. The intermediate zone 112 can be disposed between the fastening element zone 114 and the panel region 110. As shown, in some embodiments, the intermediate zone 112 can be disposed adjacent to the interface 1700 between the panel region 110 and the end region 120.

In some embodiments, the end region 120 may further comprise a grip zone 118 which is disposed between the fastening element zone 114 and the outboard end 104. The grip zone 118 can aid a user in handling the fastening member 100. For example, where the fastening member 100 is attached to a disposable diaper, the grip zone 118 can aid the user in grasping the fastening member 100 such that the overall process of fastening is facilitated. The grip zone 118 can be an extension of the end region 120 or can be a discrete component attached to the end region 120.

The fastening element zone 114 can be defined by a perimeter of the fastening element 116 which is disposed in the end region 120. The fastening element zone 114 includes all layers which are subjacent and/or superjacent to the fastening element 116. The fastening element 116 can be joined to the end region 120 by any suitable means. Exemplary means for joining the fastening element 116 to the end region are discussed hereafter with regard to FIGS. 2A-2C.

The fastening element zone 114 can have a first stiffness which can be greater than about 1000 N/m, in some embodiments. In some embodiments the first stiffness can be greater than about 1500 N/m. In some embodiments, the first stiffness can be greater than about 2500 N/m. In some embodiments, the first stiffness can be in a range from between about 1000 N/m to about 7000 N/m or any individual number within the range. In some embodiments, the first stiffness can be in a range from about 1500 N/m to about 6000 N/m. In other embodiments, the first stiffness can be in a range from about 2500 N/m to about 5000 N/m.

The stiffness of the fastening element zone 114 can provide a more stable fastening member 100 in the fastening element zone 114. For example, under an applied fastening load, typically a tension load, conventional fastening members can contract and fastening elements can buckle. However, because the fastening member 100, constructed in accordance with the present invention, comprises a fastening element zone 114 which can have a greater stiffness than a corresponding fastening element zone in a conventional fastening member, the fastening element zone 114 can be more resistant to buckling when the fastening load is applied to the fastening member 100. Because the fastening element zone 114 may be more resistant to buckling, the fastening element 116 may also be more resistant to buckling. Because of the fastening element's increased resistance to buckling, it is believed that more of the fastening element 116 can engage its target surface during fastening.

A portion of the intermediate zone 112 can have a second stiffness which can be less than the first stiffness. For example, in some embodiments, the second stiffness can be less than about 1000 N/m. In some embodiments, the second stiffness can be greater than about 200 N/m. In some embodiments, the second stiffness can be greater than about 300 N/m. In some embodiments, the second stiffness can be greater than about 400 N/m. In some embodiments, the second stiffness can be in a range from about 200 N/m to about 1000 N/m or any individual number within the range. In some embodiments, the second stiffness can be in a range from about 300 N/m to about 750 N/m. In some embodiments, the second stiffness can be in a range from about 400 N/m to about 600 N/m.

The portion of the intermediate zone 112 having the second stiffness can be disposed adjacent to the interface 1700. Additionally, in some embodiments, the portion of the intermediate zone 112 having the second stiffness can be disposed inward (toward the inboard end 102) from an inner edge 302 of the fastening element 116. For example, in some embodiments, the portion can be disposed inward (toward the inboard end 102) at least about 10% of an intermediate zone width 133 (shown in FIG. 1B) from the inner edge 302 of the fastening element 116. In some embodiments, the portion can be disposed inward (toward the inboard end 102) at least about 25% of the intermediate zone width 133 (shown in FIG. 1B) from the inner edge 302 of the fastening element 116. In some embodiments, the portion can be disposed inward (toward the inboard end 102) at least about 50% of the intermediate zone width 133 (shown in FIG. 1B) from the inner edge 302 of the fastening element 116. In some embodiments, the portion can be disposed inward (toward the inboard end 102) at least about 75% of the intermediate zone width 133 (shown in FIG. 1B) from the inner edge 302 of the fastening element 116. In some embodiments, the portion can be disposed inward (toward the inboard end 102) at least about 95% of the intermediate zone width 133 (shown in FIG. 1B) from the inner edge 302 of the fastening element 116.

The intermediate zone 112 is not limited to having only a portion with the second stiffness. In some embodiments, the entire intermediate zone 112 may comprise the second stiffness. However, in other embodiments, the intermediate zone 112 may comprise a stiffness gradient. For example, a first portion of the intermediate zone 112 proximate to the fastening element zone 114 may comprise a stiffness which is equal to the first stiffness, e.g. greater than about 1000 N/m. In contrast, a second portion of the intermediate zone 112 proximate to the interface 1700 between the panel region 110 and end region 120 may comprise a stiffness which is equal to the second stiffness, e.g. less than about 1000 N/m. A third portion of the intermediate zone 112, disposed between the first portion and the second portion can have a stiffness which is between the first stiffness and the second stiffness. As another example, the stiffness of the intermediate zone 112 may vary continuously from the inner edge 302 to the second portion of the intermediate zone 112 proximate to the interface 1700. In these embodiments, the stiffness may increase and/or decrease.

The reduced stiffness in the portion of the intermediate zone 112 can provide improved comfort for the wearer. In some embodiments, the fastening member 100 can be attached to a disposable absorbent article such that the intermediate zone 112 is positioned in a high movement area of a wearer. In these instances, an increased stiffness, e.g. greater than about 1000 N/m, can cause redmarking on the wearer because the intermediate zone of the fastening member would be more resistant to buckling. In contrast, a portion of the intermediate zone 112 of the present invention has decreased stiffness, e.g. less than about 1000 N/m, thereby allowing the portion of the intermediate zone 112 to more readily buckle instead of poking the skin of the wearer.

Additionally, in some embodiments, the panel region 110 may have a third stiffness. The third stiffness can be less than about 250 N/m, in some embodiments. In other embodiments, the third stiffness can be less than about 150 N/m. In other embodiments, the third stiffness can be less than about 100 N/m. In some embodiments, the third stiffness can be less than the second stiffness. In some embodiments, the third stiffness can be equal to the second stiffness.

One advantage of having a reduced stiffness in the panel region 110 as compared to the fastening element zone 114 is that the reduced stiffness in the panel region 110 can reduce costs for manufacturing the panel region. Typically, increased costs can be incurred as a result of increasing the amount of stiffness in a fastening member. By limiting the added stiffness to specific portions of the fastening member of the present invention, increased performance and reduced costs may be achieved.

As mentioned above, the fastening members of the present invention can be joined to a disposable absorbent article in an area which is subject to much movement of the wearer, in some embodiments. For example, fastening members of the present invention can be joined to a disposable diaper as a side panel, in some embodiments. Because the side panels are typically located in high movement areas of the disposable diaper, another advantage of having a reduced stiffness in the panel region 110, compared to the fastening element zone 114, is that the reduced stiffness panel region may conform to the wearer much easier than a stiffer material would. Additionally, because the fastening member is in a high movement area of the disposable diaper, a stiffer panel region could potentially cause redmarking on the skin of the wearer.

The fastening member 100 may further comprise a stiffening element 230 (shown in FIGS. 2A-2C and 3). The stiffening element 230 (shown in FIGS. 2A-2C and 3) can be disposed in the end region 120. The intermediate zone 112 comprises a portion of the stiffening element 230 (shown in FIGS. 2A-2C and 3). In some embodiments, the fastening element zone 114 comprises a portion of the stiffening element 230 (shown in FIGS. 2A-2C and 3). In some embodiments, the stiffening element 230 (shown in FIGS. 2A-2C and 3) may comprise the entire end region 120.

The stiffening element 230 (shown in FIGS. 2A-2C and 3) can achieve the desired first stiffness in the fastening element zone 114 and/or can achieve the desired second stiffness in the intermediate zone 112. In some embodiments, the stiffening element 230 (shown in FIGS. 2A-2C and 3) can have a stiffness of less than about 1000 N/m. In some embodiments, the stiffening element 230 (shown in FIGS. 2A-2C and 3) can have a stiffness of greater than about 200 N/m. In some embodiments, the stiffening element 230 (shown in FIGS. 2A-2C and 3) can have a stiffness of greater than about 300 N/m. In some embodiments, the stiffening element 230 (shown in FIGS. 2A-2C and 3) can have a stiffness of greater than about 400 N/m. In some embodiments, the stiffening element 230 (shown in FIGS. 2A-2C and 3) can have a stiffness in a range from about 200 N/m to about 1000 N/m or any individual number within the range. In some embodiments, the stiffening element 230 (shown in FIGS. 2A-2C and 3) can have a stiffness in a range from about 300 N/m to about 750 N/m. In some embodiments, the stiffening element 230 (shown in FIGS. 2A-2C and 3) can have a stiffness in a range from about 400 N/m to about 600 N/m.

Figure 1B:
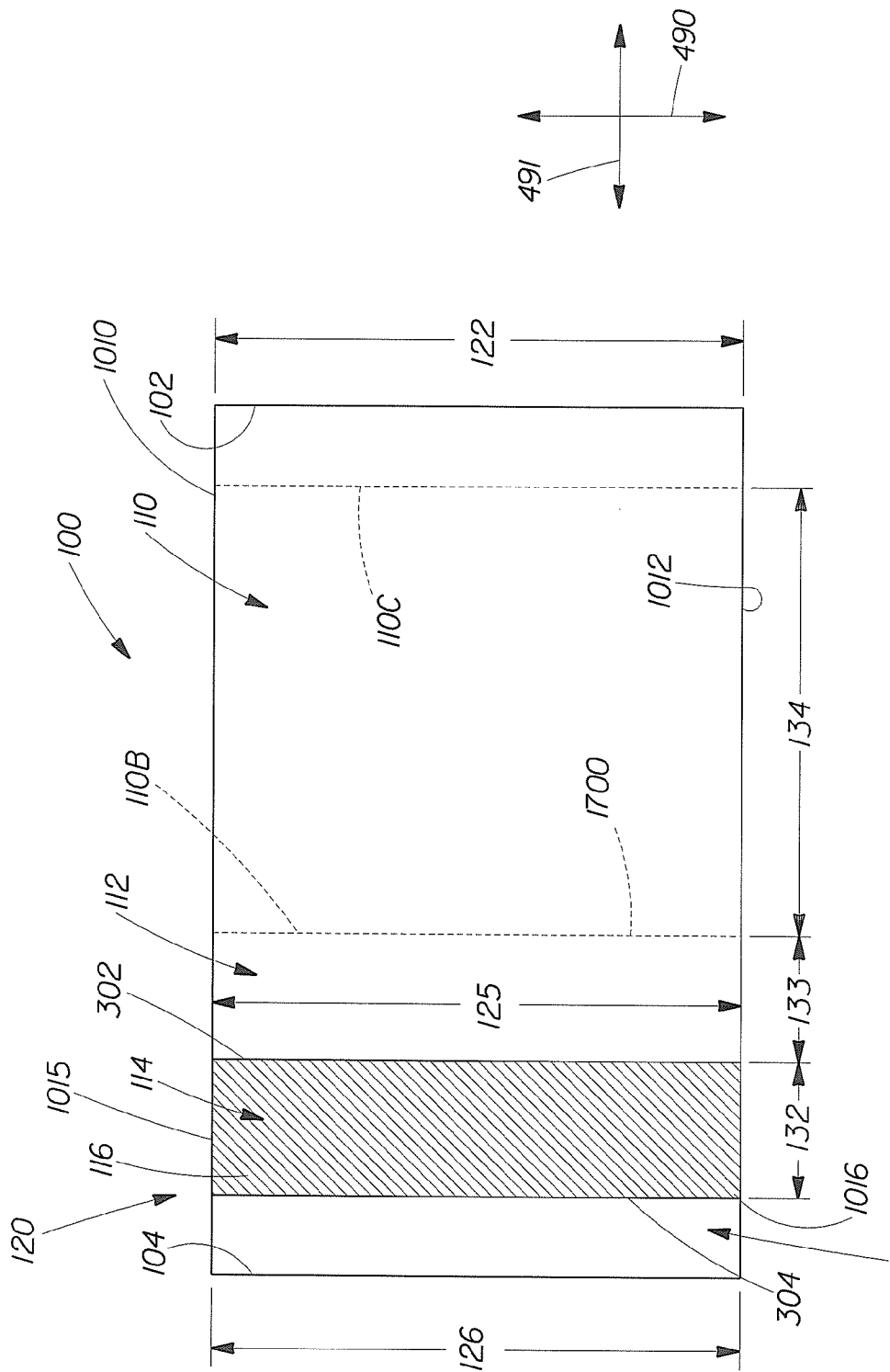
FIG. 1B is a plan view showing additional features of the fastening member of FIG. 1A.

As shown in FIG. 1B, the fastening member 100, adjacent the inboard end 102, can have a fastening member length 122. The end region 120, adjacent to the interface 1700, can have an end region length 125, and the fastening element 116 can have a fastening element length 126. The fastening member length 122 is the maximum linear distance between a leading edge 1010 and a trailing edge 1012. The end region length 125 is the maximum linear distance between the leading edge 1010 and the trailing edge 1012 adjacent to the interface 1700. The fastening element length 126 is the maximum linear distance between a first end edge 1015 and a second end edge 1016 of the fastening element 116. The maximum linear distances mentioned above are generally parallel to a first direction 490.

In some embodiments, the fastening member length 122 can be equal to the end region length 125, and the fastening element length 126 can be equal to the end region length 125. In some embodiments, the fastening element length 126 can be less than the end region length 125 which is less than the fastening member length 122. For example, the fastening element length 126 can be less than or equal to about 90% of the end region length 125. As another example, the fastening element length 126 can be less than or equal to about 80% of the end region length 125. As yet another example, the fastening element length 126 can be less than or equal to about 50% of the end region length 125. As yet another example, the fastening element length 126 can be less than or equal to about 90% of the fastening member length 122. As yet another example, the fastening element length 126 can be less than or equal to about 80% of the fastening member length 122. As yet another example, the fastening element length 126 can be less than or equal to about 50% of the fastening member length 122.

As shown, the intermediate zone 112 may have an intermediate zone width 133 and the fastening element 116 can have a fastening element width 132. The intermediate zone width 133 is the maximum linear distance between an inwardmost point 250 (shown in FIG. 2A) of a stiffening element 230 (shown in FIGS. 2A-2C and 3) and the inner edge 302 of the fastening element 116. The fastening element width 132 is the maximum linear distance between the inner edge 302 and the outer edge 304 of the fastening element 116. The maximum linear distances for the intermediate zone width 133 and the fastening element width 132, are generally parallel to a second direction 491.

In some embodiments, the intermediate zone width 133 can be greater than about zero percent of the fastening element width 132. In some embodiments, the intermediate zone width 133 can be greater than about 25% of the fastening element width 132. In some embodiments, the intermediate zone width 133 can be greater than about 50% of the fastening element width 132. In some embodiments, the intermediate zone width 133 can be greater than about 100% of the fastening element width 132.

The first direction 490 can be generally parallel to a machine direction, in some embodiments. In some embodiments, the second direction 491 can be generally parallel to a cross machine direction. In some embodiments, the second direction 491 can be generally perpendicular to the first direction 490. In some embodiments, the second direction 491 can be generally parallel to a primary direction of applied tension force, e.g. the force applied to the fastening member during fastening.

As stated previously, the perimeter of the fastening element 116 defines the fastening element zone 114. Consequently, the fastening element width 132 is also the width of the fastening element zone 114. Similarly, the fastening element length 126 is also the length of the fastening element zone 114.

The panel region 110 and the end region 120 can be separated by the interface 1700. In some embodiments, the interface 1700 can be defined, in part, by the inwardmost point 250 (shown in FIG. 2A) of the stiffening element 230 (shown in FIGS. 2A-2C and 3).

As stated previously, the fastening element zone 114 can have an increased stiffness compared to the intermediate zone 112 and, in some embodiments, when compared to the stiffness of the panel region 110. The stiffness of the fastening element zone 114 can be increased by any suitable means. Examples of suitable means of increasing the stiffness of the fastening element zone 114 are discussed with regard to FIGS. 2A-2C As shown in FIG. 2A-2C, in some embodiments, the panel region 110 may comprise a laminated structure. For example, as shown, in some embodiments, the panel region 110 may comprise a first substrate 202 and a second substrate 204. The first substrate 202 and the second substrate 204 can be joined together in a face-to-face orientation. The first substrate 202 and the second substrate 204 can be joined together by a first bonding agent 216 and/or a second bonding agent 217.

The end region 120 may also comprise a laminated structure. For example, the end region 120 may comprise the stiffening element 230 and the fastening element 116. Additionally, the end region 120 further comprises at least a portion of the first substrate 202 and/or the second substrate 204. The stiffening element 230 can be disposed between the first substrate 202 and the second substrate 204.

The stiffening element 230 may comprise a first portion 260 and, in some embodiments, a second portion 265 (shown in FIG. 2B). The first portion 260 can be disposed adjacent to the panel region 110 while the second portion 265 can be disposed adjacent to the outboard end 104. The first portion 260 may have a first portion width 280 which is the maximum linear distance generally parallel to the second direction 491 between the inwardmost point 250 of the stiffening element 230 and an outwardmost point 251 of the second bonding agent 217 or an outwardmost point 252 of the first bonding agent 216 whichever is less. In some embodiments, the first portion width 280 may extend all the way out to the outboard end 104 as shown in FIG. 2A. In the embodiments of the present invention, the first portion 260 can be secured between the first substrate 202 and the second substrate 204 by the first bonding agent 216, the second bonding agent 217, and/or any other suitable means.

As shown in FIG. 2A, in some embodiments, the fastening element 116 can be joined to the second substrate 204 by a third bonding agent 218. As shown, in FIGS. 2B and 2C, in some embodiments, the fastening element 116 can be joined to the stiffening element 230 by the third bonding agent 218.

As shown in FIG. 2A, in some embodiments, the first substrate 202 and/or the second substrate 204 may extend outward from the inboard end 102 to the outboard end 104 such that the first substrate 202 and/or the second substrate 204 comprise the entire end region 120. In some embodiments, where both the first substrate 202 and the second substrate 204 comprise the entire end region 120, the first portion 260 may comprise the entire stiffening element 230.

In contrast, as shown in FIG. 2B, in some embodiments, the first substrate 202 and/or the second substrate 204 can extend outward from the inboard end 102 such that the first substrate 202 and/or the second substrate 204 comprise a portion of the end region 120 but not the entire end region 120. For example, as shown, the intermediate zone 112 may comprise a portion of the first substrate 202 and/or the second substrate 204 yet, the fastening element zone 114 may not comprise the first substrate 202 and/or second substrate 204. As another example, the first substrate 202 and/or the second substrate 204 may extend outward from the inboard end 102 such that the intermediate zone 112 and the fastening element zone 114 each comprise a portion of the first substrate 202 and/or the second substrate 204.

As shown, in some embodiments, the first bonding agent 216 and/or the second bonding agent 217 may extend from the inboard end 102 toward the outboard end 104 overlapping a portion of the end region 120. In some embodiments, the first bonding agent 216 and/or the second bonding agent 217 overlap at least the first portion 260 of the stiffening element 230 such that the stiffening element 230 is joined to the first substrate 202 and the second substrate 204.

As shown in FIG. 2C, in some embodiments, the first substrate 202 can extend from the inboard end 102 to the outboard end 104 such that the first substrate 202 comprises the entire end region 120. The first bonding agent 216 can similarly extend from the inboard end 102 to the outboard end 104 such that first bonding agent 216 comprises the entire end region 120. In contrast, as shown, in some embodiments, the second bonding agent 217 can extend from the inboard end 102 into the end region 120 such that the second bonding agent 217 overlaps a portion of the intermediate zone 112. Similarly, in some embodiments, the second substrate 204 can be configured as described above with regard to FIG. 2B.

The stiffening element 230 may be any suitable size. For example, the stiffening element 230 may overlap the entire end region 120. As another example, the first portion 260 of the stiffening element 230 can be disposed between the first substrate 202 and the second substrate 204 and extend outward such that the stiffening element 230 comprises part of the fastening element zone 114. In some embodiments, the stiffening element 230 can extend inward from the outboard end 102 to the inboard end 102 such that the stiffening element 230 comprises the entire panel region 110.

An advantage of the present invention is that the first portion 260 of the stiffening element 230 is disposed between and is joined to the first substrate 202 and to the second substrate 204. Because the first portion 260 is joined to the first substrate 202 and to the second substrate 204, edges of the first portion 260 are secured between the first substrate 202 and the second substrate 204. So, the edges of the stiffening element 230 are less likely to be exposed when the fastening member is under tension.

The first portion width 280 can be of any suitable size. For example, in some embodiments, the first portion width 280 can be greater than about 2% of the intermediate zone width 133. In some embodiments, the first portion width 280 can be between about 2% and 100% of the intermediate zone width 133 or any individual number within the range. In some embodiments, the first portion width 280 can be between about 10% and 75% of the intermediate zone width 133. In some embodiments, the first portion width 280 can be between about 25% and 50% of the intermediate zone width 133. In some embodiments, the first portion width 280 may be greater than or equal to the fastening element width 132 in addition to the intermediate zone width 133. In some embodiments, the first portion width 280 can be equal to an end region width. In some embodiments, the first portion width 280 can be greater than about 1 mm and less than or equal to about 50 mm or any individual number within the range. In some embodiments, the first portion width 280 can be greater than or equal to about 4 mm and less than or equal to about 35 mm. In some embodiments, the first portion width 280 can be greater than or equal to about 8 mm and less than or equal to about 25 mm.

Figure 8:
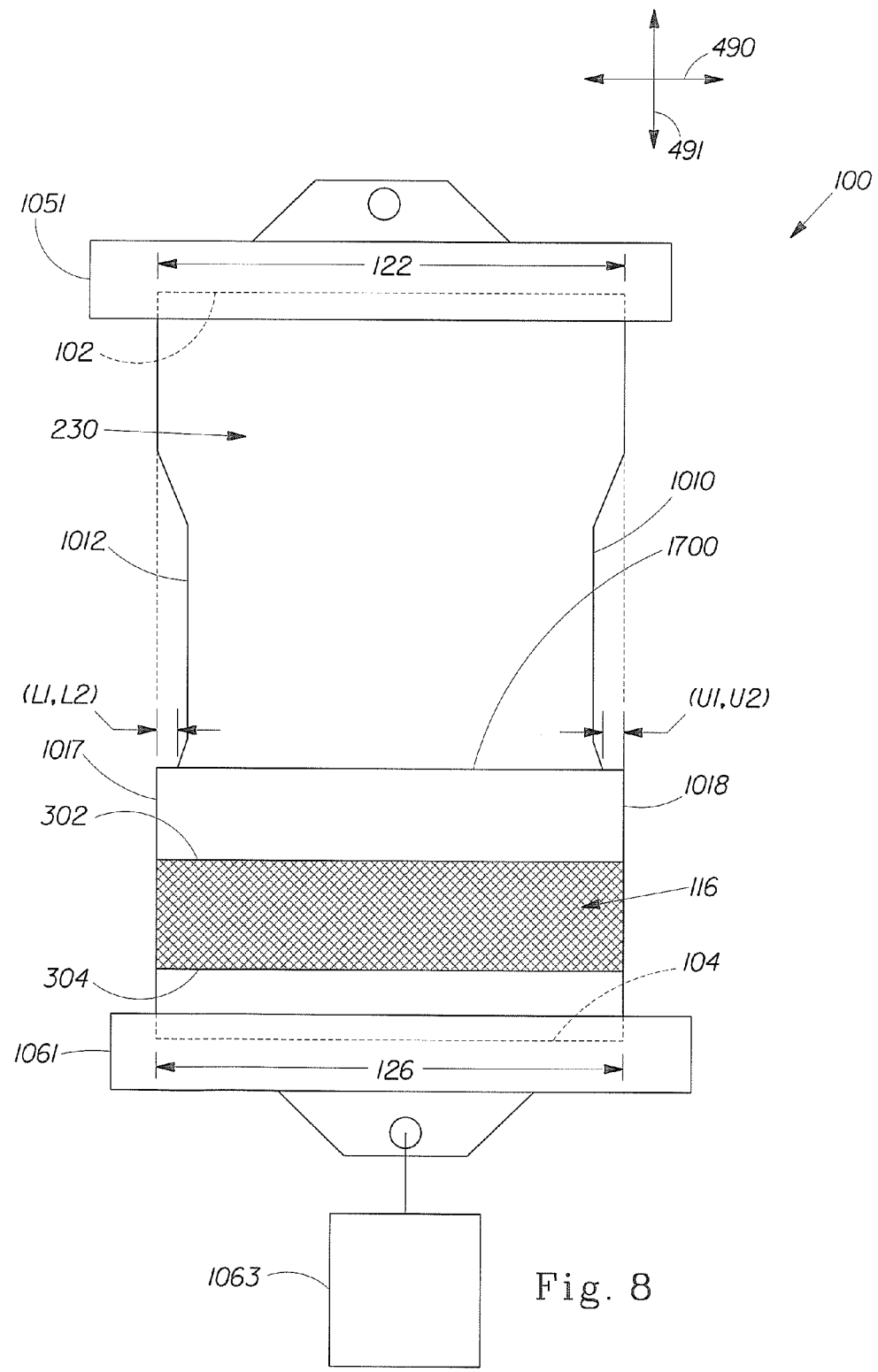
FIG. 8 is an elevation view showing the measurement of exposed edges of a stiffening element in a fastening member.

In some embodiments, under a tension of between 1.5 N/cm and 4.0 N/cm, edges of the stiffness element 230 in the first portion 260 are exposed less than about 1 mm. In some embodiments, the edges of the stiffness element 230 have an exposed edge length measurement of less than about 2 mm. As shown in FIG. 8, exposed edge length is the maximum distance generally parallel to the first direction 490 between a first edge 1018 of the stiffening element 230 and the leading edge 1010. Alternatively, exposed edge length can be the maximum distance generally parallel to the first direction 490 between a second edge 1017 of the stiffening element 230 and the trailing edge 1012. The test method for measuring exposed edge length is hereafter. In some embodiments, the edges of the stiffness element 230 in the first portion 260 are exposed less than about 0.5 mm. In some embodiments, the edges of the stiffness element 230 have an exposed edge length of less than about 0 mm.

In some embodiments, a ratio of the amount of exposed edges of the stiffness element 230 to the end region length 125 defines an exposure ratio and can be between about 0% to about 10% or any individual number within the range. In some embodiments, the exposure ratio can be less than or equal to about 5%. In some embodiments, the exposure ratio can be less than or equal to about 3%. In some embodiments, the exposure ratio can be less than or equal to about 2%. In some embodiments, the exposure ratio can be less than or equal to about 1%.

In some embodiments, a exposure ratio of the amount of exposed edges of the stiffness element 230 to the fastening element length 126 can be between about 0% to about 10% or any individual number within the range. In some embodiments, the exposure ratio can be less than or equal to about 5%. In some embodiments, the exposure ratio can be less than or equal to about 3%. In some embodiments, the exposure ratio can be less than or equal to about 2%. In some embodiments, the exposure ratio can be less than or equal to about 1%.

As stated previously, the panel region can be elastically extensible in some embodiments. In embodiments where the panel region is elastically extensible, a fastening member constructed in accordance with the present invention may comprise an elastomeric element. An example of such an embodiment is discussed with regard to FIG. 3.

Figure 3:
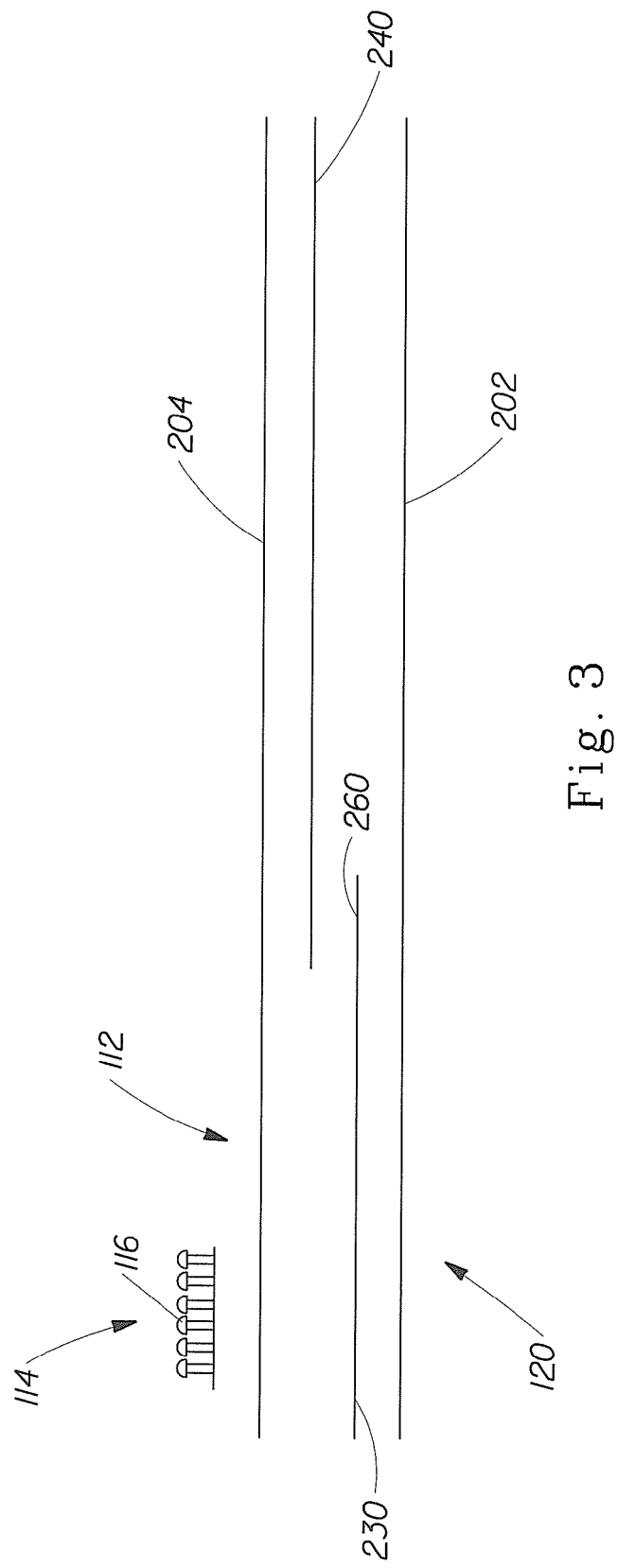
FIG. 3 is a cross sectional view showing another embodiment of the fastening member of FIG. 1A.

As shown in FIG. 3, the panel region 110 may comprise, in addition to the first substrate 202 and the second substrate 204, an elastomeric element 240. The elastomeric element 240 can be sandwiched between the first substrate 202 and the second substrate 204. Although not shown, the elastomeric element 240 can be joined to the first substrate 202 and/or the second substrate 204 by the first bonding agent 216, the second bonding agent 217, and/or any other suitable means.

As shown, in some embodiments, the stiffening material 230 can be disposed between the elastomeric element 240 and the first substrate 202. In other embodiments, the stiffening element 230 can be disposed between the elastomeric element 240 and the second substrate 204. Additionally, despite the fact that FIG. 3 shows the first substrate 202 and/or the second substrate 204 comprising the entire end region 120, the first substrate 202 and/or the second substrate 204 can be configured as discussed previously with regard to FIGS. 2A-2C. In embodiments where the stiffening element 230 overlaps a portion of the elastomeric element 240, a bonding agent can be disposed between the stiffening element 230 and the elastomeric element 240.

Additionally, as shown, in some embodiments, the elastomeric element 240 can extend from the inboard end 102 to the end region 120 such that only a portion of the end region 120, e.g. the intermediate zone 112, comprises a portion of the elastomeric element 240. In other embodiments, the elastomeric element 240 can extend from the inboard end 102 to the outboard end 104 such that the elastomeric element 240 comprises the entire end region 120. In other embodiments, the elastomeric element 240 can extend from the inboard end 102 to the end region 120 such that the intermediate zone 112 and the fastening element zone 114 each comprise a portion of the elastomeric element 240.

The fastening members of the present invention may comprise a wide variety of materials. For example, the first substrate 202 and/or the second substrate 204 may comprise a woven, nonwoven, film, a laminate, the like, or any combination thereof. In some embodiments, the first substrate 202 and/or the second substrate 204 may be extensible and/or elastically extensible. Where the first substrate 202 and/or the second substrate 204 comprise a nonwoven, any suitable nonwoven can be used. In some embodiments, the nonwoven may comprise one layer of fibers. In other embodiments, the nonwoven may comprise more than one layer of fibers. Any suitable nonwoven can be used. For example, a suitable nonwoven may comprise fibers made of polypropylene, polyethylene, polyester, nylon, cellulose, polyamide, or combinations of such materials. Fibers of one material or fibers of different materials or material combinations may be used in the first and/or second nonwoven. Exemplary nonwoven materials include spunbond, spunbond meltblown spunbond (SMS), spunbond meltblown meltblown spunbond (SMMS), carded, meltblown, and the like. Particularly acceptable nonwovens include high elongation carded (HEC) nonwovens and deep activation polypropylene (DAPP) nonwovens. Any process known in the art may be used to make the nonwovens.

The nonwoven may comprise fibers that are bonded mechanically, including fibers that are needle punched or hydro entangled. Other suitable bonding processes for producing a suitable nonwoven for use in the present invention are spun bonding, thermally bonding, bonding by various types of chemical bonding such as latex bonding, powder bonding, and the like.

In certain embodiments, the basis weight of the nonwoven can be in the range of about 10 gsm to about 100 gsm or any individual number within the range. In other embodiments, the basis weight of the nonwoven can be in a range of about 40 gsm to about 80 gsm. In yet other embodiments, the basis weight of the nonwoven can be in a range of about 50 gsm to about 60 gsm. The basis weights of the substrates of the present invention can be any suitable basis weight.

The fibers may be of any suitable size and shape. In some embodiments, the fiber may have a denier ranging from about 1 to about 10 or any individual number within the range. In some embodiments, the denier of the fibers can range from about 1 to about 8. In other embodiments, the denier of the fibers can range from about 1 to about 5.

The elastomeric element 340 may comprise any suitable elastic known in the art. Suitable elastomeric elements may comprise a wide variety of materials as are well known in the art. Some examples include elastomeric films, polyurethane films, elastomeric foams, formed elastic scrim and synthetic elastomers (e.g., Lycra™). A suitable elastomeric element 240 for use in conjunction with the present invention may comprise elastic strands and/or elastic films. Any suitable elastic film known in the art can be used. Suitable elastic films may comprise polypropylene, polyethylene, polyolefins, styrene-isoprene-styrene, styrene-butadiene-styrene, or combinations thereof. The basis weight of the films can range from about 10 gsm to about 100 gsm.

Alternatively, or in conjunction with the elastic film, the elastomeric element 340 may further comprise elastic strands. Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges, or other sections of circles or ellipses, other polygons, or other irregular enclosed shapes. Furthermore, the thickness or diameter of the elastic strands may vary in order to accommodate a particular application. Typically, the thickness of elastic strands may be in the range of about 0.02 mm to about 1 mm and the basis weight is in the range of about 20 g/m2 to about 300 g/m2. The elastic strands may be applied separately to the substrate, can be extruded onto the substrate, or can be printed onto the substrate.

Suitable apparatuses and methods for printing elastomeric elements in any orientation are described in U.S. Application Publication No. 2004/0181200; U.S. Application Publication No. 2004/0193133; and WO 2005/110731 A3. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 $g/m^2$ to about 300 $g/m^2$.

The first bonding agent 216, the second bonding agent 217, and/or the third bonding agent 218, may comprise any suitable bonding agent known in the art. For example, in some embodiments, at least one of the bonding agents may comprise an adhesive. Any suitable adhesive can be used in the present invention. For example, the adhesive may comprise styrene-olefin-styrene triblock copolymers such as styrene-isoprene-styrene, styrene-butadiene-styrene, the like, or combinations thereof.

An example of a suitable bonding agent for joining the fastening element 116 to the stiffening element 230 and/or the second substrate 204 is an adhesive made from Bostik located in Wauwatosa, Wis., having a model number H2988-F02. In some embodiments, the fastening element 116 can be joined to the stiffening element 230 and/or the second substrate 204 via the bonding agent plus mechanical bonds, fusion bonds, the like, or any combination thereof. In some embodiments, the fastening element 116 can be joined to the stiffening element 230 and/or the second substrate 204 via mechanical bonds, fusion bonds, or the like, or any suitable combination thereof.

In some embodiments, at least one of the bonding agents may comprise a polymer. Any suitable polymer known in the art can be utilized. Some examples of suitable polymers include a high modulus hot melt polymer, or may include a molten polymer. Any suitable molten polymer can be used. Some examples of molten polymers include polyethylene, polypropylene, the like, or any suitable combinations thereof.

In some embodiments, the basis weight of the first bonding agent 216, the second bonding agent 217, and/or the third bonding agent 218 in the fastening element zone 114 can be greater than or equal to about 30 gsm. In other embodiments, the first bonding agent 216, the second bonding agent 217, and/or the third bonding agent 218 in the fastening element zone 114 can have a basis weight of greater than or equal to about 60 gsm. In some embodiments, first bonding agent 216, the second bonding agent 217, and/or the third bonding agent 218 in the fastening element zone 114 can have a basis weight of greater than or equal to about 100 gsm.

The stiffening material 230 can be any suitable stiffening material known in the art. Some examples of suitable stiffening materials 230 include webs of any type, e.g. woven, nonwoven, laminates, natural or synthetic materials including polypropylene, polyethylene, poly(ethylene terephthalate), nylon, paper, cellulose, styrene-isoprene-styrene, styrene-butadiene-styrene block copolymers, the like, or any suitable combination thereof. Some examples of suitable laminates include bilaminates of film and nonwoven such as M18-750 or M18-1018 manufactured by Clopay Corporation, Cincinnati, Ohio. An example of a suitable nonwoven is Typar SBPP3301Y manufactured by BBA Fiberweb™, located in Brentwood, Tenn.

The fastening members of the present invention, as discussed previously, can be utilized in a number of consumer goods. For example, the fastening members of the present invention can be joined to a disposable diaper. An example of such an embodiment is shown in FIG. 4A.

Figure 4A:
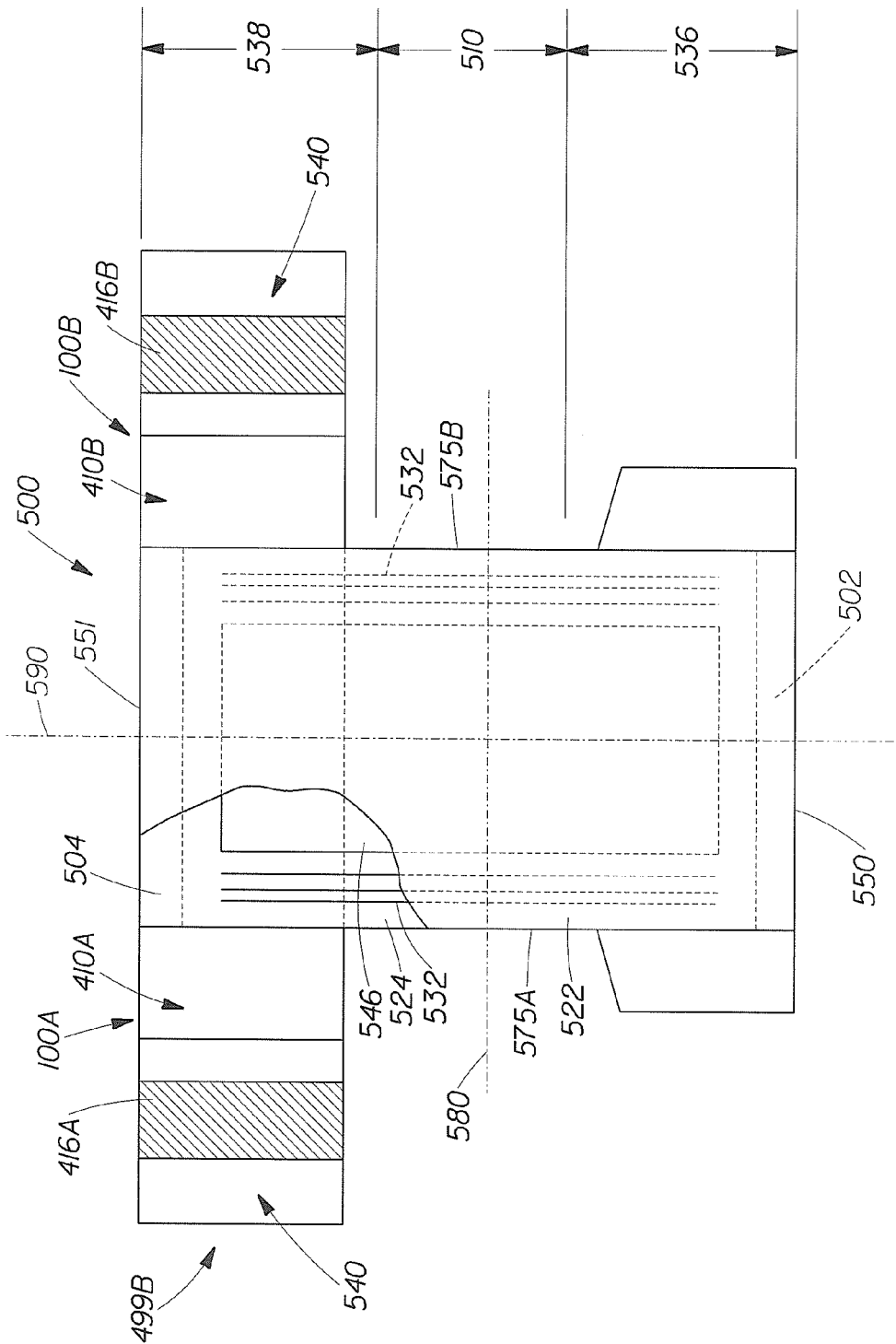
FIG. 4A is a plan view showing a disposable diaper comprising fastening members constructed in accordance with the present invention.

As shown in FIG. 4A, in some embodiments, fastening members 100A and 100B constructed in accordance with the present invention can be joined to a disposable diaper 500. The fastening members 100A and 100B can be configured similarly to the fastening members discussed heretofore.

The fastening members 100A and 100B can be joined to the disposable diaper 500 adjacent to their respective inboard ends 102A and 102B. As shown in FIG. 4A, the disposable diaper 500 may comprise a liquid pervious topsheet 522 and a backsheet 524 joined to at least a portion of the topsheet 522. The disposable absorbent article 500 further comprises an absorbent core 546 positioned between the topsheet 522 and the backsheet 524. The disposable diaper 500 may further comprise elastic leg features 532, a first waist member 502 and a second waist member 504.

A portion of the periphery of the disposable diaper 500 can be defined by the longitudinal edges 575A and 575B; a first waist edge 550, and the second waist edge 551. The longitudinal edges 575A and 575B can run generally parallel to a longitudinal centerline 590 of the disposable absorbent article 500. The first waist edge 550 and the second waist edge 551 can run generally parallel to a lateral centerline 580 of the disposable diaper 500.

The first waist member 502 and/or the second waist member 504 can be elastically extensible. As shown, in some embodiments, the first waist member 502 can be disposed adjacent the first waist edge 550. In some embodiments, the second waist member 504 can be disposed adjacent to the second waist edge 551. Generally, the first waist member 502 and/or the second waist member 504 can be under tension prior to being joined to the disposable diaper 500. So, upon release of at least a portion of the tension applied to the first waist member 502 and/or the second waist member 504, a portion of the disposable diaper 500 joined thereto can corrugate. This corrugation of the disposable diaper 500 can allow the first waist member 502 and/or the second waist member 504 and the disposable diaper 500 to expand and contract about the waist of a wearer, thereby providing more comfort and improved fit to a wearer. Examples of suitable waist members 502 and/or 504 include those described in U.S. Pat. Nos. 4,515,595; 5,151,092; and 5,221,274. Although disposable diapers are generally constructed so as to have two elastic waist features, one positioned in a first waist region and one positioned in a second waist region, diapers can be constructed with a single elastic waist feature.

The disposable diaper 500 may further comprise outer cuffs and inner cuffs to improve containment of liquids and other body exudates. Each elasticized outer cuff may include several different embodiments for reducing the leakage of body exudates in the leg regions. Outer cuffs and inner cuffs are further described in U.S. Pat. Nos. 3,860,003; 4,909,803; and 4,695,278.

As stated previously, the disposable diaper 500 may further comprise the fastening members 100A and 100B. The fastening members 100A and 100B can be joined to the disposable diaper 500 such that a portion of the panel region 410A and a portion of the panel region 410B can extend outward from the first longitudinal edge 575A and the second longitudinal edge 575B of the disposable diaper 500, respectively. In some embodiments, the fastening members 100A and 100B can be joined to the disposable diaper 500 in a second waist region 538, and in some embodiments, the fastening members 100A and 100B can be joined to the disposable diaper 500 in a first waist region 536.

Alternatively, in some embodiments, the disposable diaper 500 may comprise fastening members in the second waist region 538 and fastening members disposed in the first waist region 536. In these embodiments, at least one of the fastening members in the first waist region and/or the fastening members in the second waist region comprise complimentary fastening elements. For example, the fastening members in the second waist region may include fastening elements which comprise engaging components while the fastening members in the first waist region may include fastening elements which comprise receiving components. Any suitable combination of complementary fastening elements can be used.

Figure 4B:
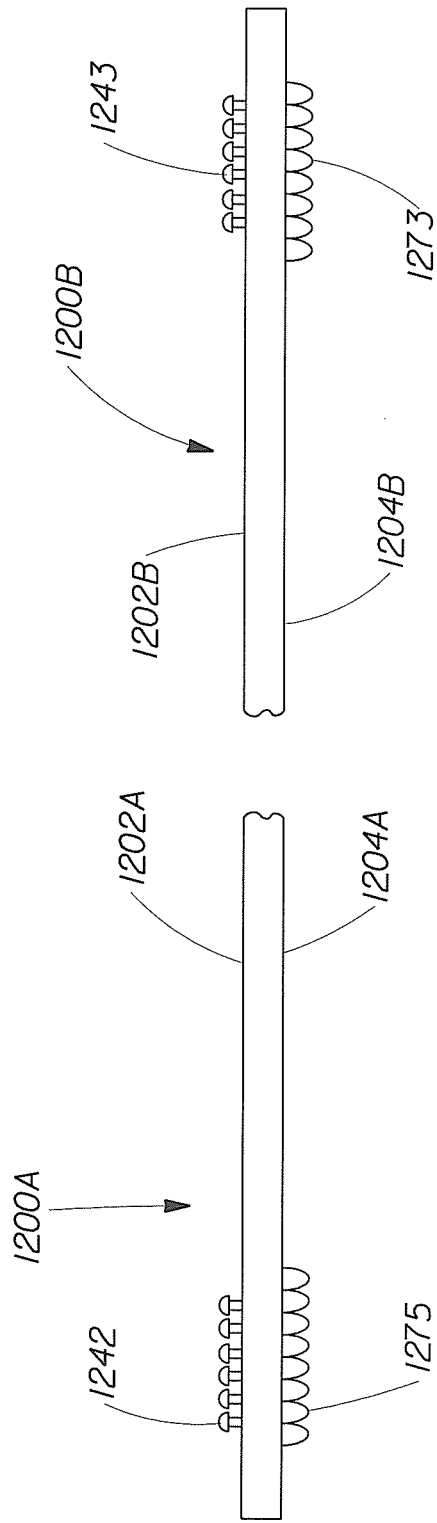
FIG. 4B is a plan view showing another embodiment for the fastening members of FIG. 8A.

In some embodiments, the disposable diaper 500 may comprise fastening members having a plurality of fastening members as shown in FIG. 4B. As shown, in some embodiments, fastening members 1200A and 1200B may comprise a plurality of fastening elements. For example, fastening member 1200A can include an engaging component 1242 having a plurality of engaging elements. The engaging component 1242 can be disposed on a first surface 1202A of the fastening member 1200A. The fastening member 1200A may further comprise a receiving component 1275 which can be disposed on a second surface 1204A of the fastening member 1200A, in some embodiments. The second surface 1204A can be opposite to the first surface 1202A.

Similarly, the second fastening member 1200B may comprise an engaging component 1243 disposed on a first surface 1202B and a receiving component 1273 disposed on a second surface 1204B, in some embodiments. One advantage of this arrangement is that the engaging components 1242 and 1243 can engage a receiving component disposed on the disposable diaper 500 (shown in FIG. 4A) or can join to the receiving components 1275 and 1273 on the other fastening member. For example, in some embodiments the engaging component 1242 can join the receiving component 1273 when fastened. In other embodiments, the engaging component 1243 can join the receiving component 1275 when fastened.

Referring to FIG. 4A, in some embodiments, the fastening members 100A and 100B can form a portion of the leg openings when the disposable diaper 500 is fastened. The fastening members 100A and 100B can form a portion of the leg openings which would be disposed on an outer surface of a leg of a wearer. A crotch region 510 of the disposable diaper 500 in conjunction with the first waist region 536 and the second waist region 538 can form a portion of the leg openings which would be disposed on an inner surface of the leg of the wearer.

In some embodiments, the fastening members 100A and 100B can be joined to an outer-facing surface of the backsheet 524. In some embodiments, the fastening members 100A and 100B can be joined to a wearer-facing surface of the topsheet 522. In some embodiments, the fastening members 100A and 100B can be joined to the disposable diaper 500 between the topsheet 522 and the backsheet 524. The fastening members 100A and 100B can be joined to the disposable diaper 500 in any suitable configuration or location.

The disposable diaper 500 further comprises a fastening system 540 which joins at least a portion of a first waist region 536 with at least a portion of a second waist region 538, preferably to form leg and waist openings. The fastening system 540 also works with the waist members(s) 502 and/or 504 to maintain lateral tension in order to keep the disposable absorbent article 500 in place about the waist of the wearer. The fastening system 540 may comprise fastening elements 416A and 416B which, in some embodiments, can be disposed on the fastening members 100A and 100B. The fastening system 540 may further comprise a receiving component which, in some embodiments, is disposed in the first waist region 536 of the disposable diaper 500. The fastening element 416A and 416B can be configured to engage the receiving component thereby joining the first waist region 536 and the second waist region 538 of the disposable diaper 500.

Any suitable fastening elements known in the art can be used in the present invention. Examples of suitable fastening elements include engaging components, receiving components, adhesive components, cohesive components, the like, or any suitable combination thereof.

An example of a suitable engaging component may comprise hook fastening material. The hook fastening material can mechanically engage fibrous elements of a receiving element so as to provide a secure closure. A hook fastening material according to the present invention may be manufactured from a wide range of materials. Examples of suitable materials include nylon, polyester, polypropylene, or any combination of these materials, or other materials as are known in the art.

A suitable hook fastening material comprises a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087. In some embodiments, the hooks can be thermoplastically printed. Examples of suitable hook printing processes are described in U.S. Pat. No. 5,540,673 and in WO 2004/082918.

An example of a suitable receiving component may comprise a plurality of loops. Loop fastening material and a method for making the same are described in U.S. Pat. Nos. 5,380,313 ; 5,569,233; 5,407,439; 5,542,942; 5,669,900; 5,318,555; U.S. Application Publication No. 2003/0077430; and WO 04/030763.

An example of a suitable adhesive component may comprise discrete tape tabs. An example of a suitable tape tab is available from the 3M Corporation of St. Paul, Minn., U.S.A. under the designation XMF99121.

An example of a suitable cohesive component may comprise cohesive fastening patches. In some embodiments, the cohesive fastening patches may be formed of an inherently crystalline water-based synthetic elastomer to which a tackifying agent has been added to disrupt the polycrystalline structure and thereby render the elastomer cohesive. Exemplary synthetic cohesive products are available from Andover Coated Products, Incorporated, of Salisbury, Mass., U.S.A. and are described in U.S. Pat. No. 6,156,424.

Disposable diapers may comprise many components, elements, members, etc. and can be constructed in a variety of manners. For example, the topsheet and the backsheet can have length and width dimensions generally larger than those of the absorbent core. The topsheet and the backsheet can extend beyond the edges of the absorbent core, thereby forming the periphery of the disposable absorbent article. The topsheet, the backsheet, and the absorbent core may include many different materials and may be assembled in a variety of well known configurations, exemplary diaper materials and configurations are described generally in U.S. Pat. Nos. 3,860,003; 5,151,092; and 5,221,274.

Any topsheet compatible with the present invention which is known in the art can be used in the present invention. A suitable material for a topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. As an example, a material suitable for use in a topsheet comprises a web of staple-length polypropylene fibers is manufactured by Veratec, Inc., a Division of International Paper Company, of Walpole, Mass. under the designation P-8.

Some examples of suitable topsheets are described further in U.S. Pat. Nos. 3,929,135; 4,324,246; 4,342,314; 4,463,045; 5,006,394; 4,609,518; 4,629,643. Any portion of the topsheet may be coated with a lotion as is known in the art. Examples of suitable lotions include those described in U.S. Pat. Nos. 5,607,760; 5,609,587; 5,635,191; 5,643,588; 5,968,025; 6,716,441; and PCT Publication No. WO 95/24173. Further, the topsheet may be fully or partially elastically extensible or may be foreshortened so as to provide a void space between the topsheet and the absorbent core. Exemplary structures including elasticized or foreshortened topsheets are described in more detail in U.S. Pat. Nos. 4,892,536; 4,990,147; 5,037,416; and 5,269,775.

A suitable backsheet for use in the disposable absorbent article of the present invention may comprise a laminated structure. For example, the backsheet may comprise a first backsheet layer and a second backsheet layer. The second backsheet layer can be impervious to liquids (e.g., urine) and comprise a thin plastic film such as a thermoplastic film having a thickness, for example, of about 0.012 mm (0.5 mils) to about 0.051 mm (2.0 mils). Suitable backsheet films include those manufactured by Tredegar Corporation, based in Richmond, Va., and sold under the trade name CPC2 film. Either the first backsheet layer and/or the second backsheet layer may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. Nos. 5,938,648; 5,865,823; and 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Suitable exemplary absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; and 5,625,222.

The backsheet may be joined to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. Nos. 4,573,986; 3,911,173; 4,785,996; and 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on disposable absorbent article or may be one or more separate elements joined directly or indirectly with one or more elements of the disposable absorbent article. Further, the sublayer may include a structure that is separate from the absorbent core or may include or be part of at least a portion of the absorbent core.

Suitable exemplary materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials deposited in the pull-on disposable absorbent article, and the like, or any combinations thereof. Examples of pockets and spacers for use in absorbent products are described in U.S. Pat. No. 5,514,121; 5,171,236; 5,397,318; 5,540,671; 6,168,584; 5,306,266; and 5,997,520. Examples of compartments or voids in an absorbent article are disclosed in U.S. Pat. Nos. 4,968,312; 4,990,147; 5,062,840; and 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. Nos. 5,941,864; 5,977,430; and 6,013,063.

Embodiments of the present invention may include acquisition/distribution layers which can be configured to distribute moisture from a wetness event to moisture responsive members within the disposable absorbent article. Examples of suitable acquisition/distribution layers are described in U.S. Pat. No. 5,460,622, U.S. Patent Application Publication No. 2005/0027267, and U.S. Patent Application Publication No. 2005/009173.

Embodiments of the present invention may include a dusting layer which is well known in the art. Examples of suitable dusting layers are discussed in U.S. Pat. No. 4,888,231.

Test Methods:
Extensibility

Force at elongation is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with diamond faced grips, wider than the width of the test specimen.

Equilibrate samples in a conditioned room maintained at about 23±2° C. and about 50±2% relative humidity for at least two hours before testing. Herein width of the sample is defined as dimension 491 and length is defined as dimension 490 according to FIG. 1B.

Choose two matching fastening members 100 and label them Specimen A and Specimen B. On Specimen A, determine and mark the proximal edge of the stiffening element at 110B. Determine and mark the proximal edge of the stretch region 110C. For example, marks can be placed 1 mm apart along the width of the stretch region where the 110C boundary is suspected to be. By hand, gently (<20 gf) pull 1 cm segments along that edge to detect the boundary where the marks remain at 1 mm and where they spread apart. Measure the width of the stretch region 134 to the nearest 1 mm. Using a scalpel, cut a strip 2.54 mm long 490 from the center of specimen that extends its entire width 491. Trim the width 491 of the strip leaving at least 5 mm extending from both ends 110B and 110C to clamp in the grip faces. On the matching Specimen B, once again determine and mark the proximal edge of the stiffening element at 110B. Measure the distance 133 from 110B to the proximal edge of the fastening element 302 to the nearest 1 mm. Using a scalpel, cut a strip 2.54 mm long 490 from the center of specimen that extends its entire width 491. Trim the width 491 of the strip leaving at least 5 mm extending from both ends 302 and 110B to clamp in the grip faces.

Set the gauge length of the tensile tester to distance 134. Zero the crosshead and load the cell. Insert Specimen A into the upper grips aligning it along 110B and close the upper grips. Insert the specimen into the lower grips aligning it along 110C and close. The specimen should be aligned vertically without skew, and under enough tension to eliminate any slack, but less than 0.05N of force on the load cell. Start the tensile tester and data collection. The jaws are moved apart at a rate of 127 mm/min to the desired % elongation. Herein, % Elongation is defined as the extension divided by the gauge length, multiplied by 100. Reset the gauge length to distance 133 and run Specimen B in like fashion aligning the specimen at 302 and 110B in the grips.

The force at the desired % elongation is calculated by the software from the resulting force/elongation curves. Results are calculated as Force in Newtons at the target elongation divided by the length (direction 490) of the specimen in mm, and reported to the nearest 0.01 N/mm.

Stiffness

Figure 6A:
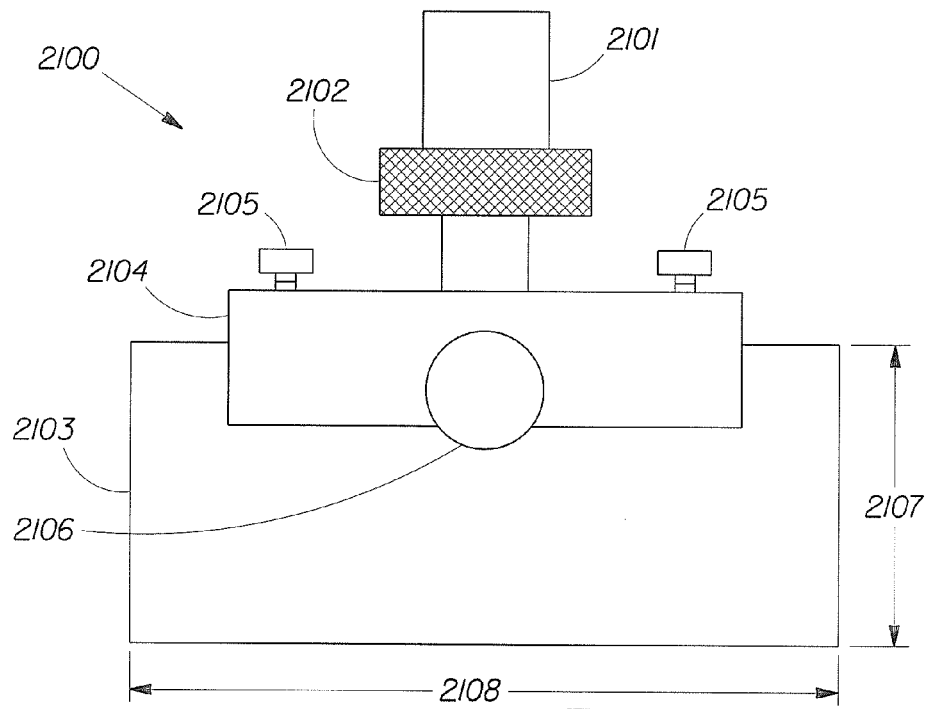
FIG. 6A is a front elevation view showing a plunger for use with the apparatus of FIG. 5.
Figure 6B:
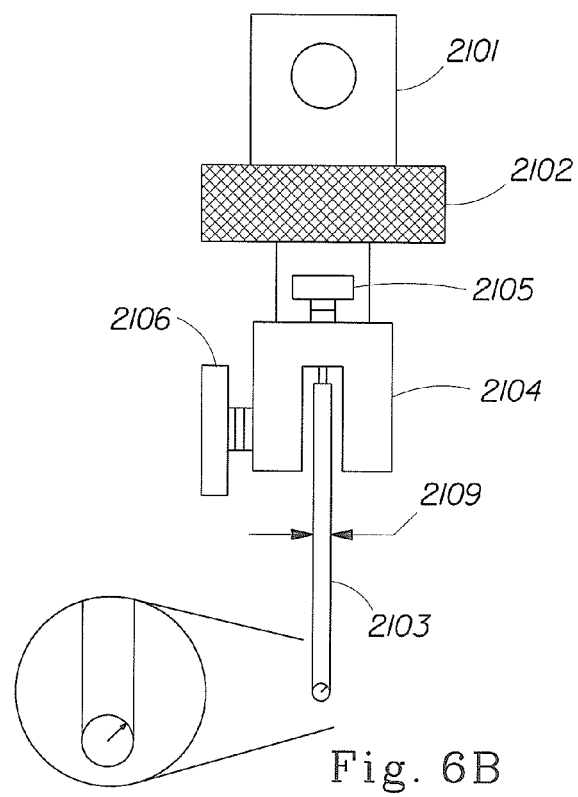
FIG. 6B is a side elevation view showing a plunger for use with the apparatus of FIG. 5.

Stiffness is measured using a constant rate of extension tensile tester with computer interface (a suitable instrument is a MTS Alliance under TestWorks 4 software, as available from MTS Systems Corp., Eden Prairie, Minn.) fitted with a 10 N load cell. A plunger blade 2100, shown in FIG. 6A (front view) and FIG. 6B (side view), is used for the upper movable test fixture. Base support platforms 2200, shown in FIG. 6, are used as the lower stationary test fixture. All testing is performed in a conditioned room maintained at about 23° C.±2° C. and about 50%±2% relative humidity. Herein, width of the sample is defined as dimension 491 and length is defined as dimension 490 according to FIG. 1B.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 8.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm. Set the crosshead to lower at 500 mm/min for a distance of 25 mm. Set the data acquisition rate to 200 Hz.

Figure 5:
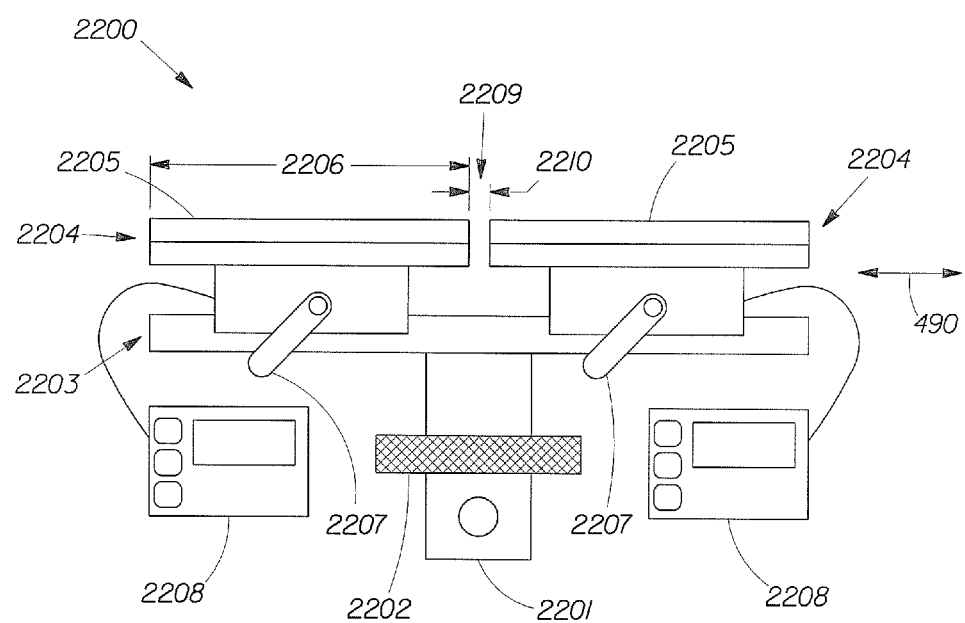
FIG. 5 is an elevation view showing an apparatus for testing the stiffness of materials.

Precondition samples at about 23° C.±2° C. and about 50%±2% relative humidity for 2 hours prior to testing. Die cut a test specimen 13 mm in width (direction 491) by 25.4 mm in length (direction 490). If the element is not 13 mm in width, use the full width of the element. Examine the specimen for any exposed adhesive and deactivate by applying baby powder where necessary. Place the specimen flat onto the surface of the support platform 2204 over the gap 2209 with the fastening element facing upward. If the particular specimen does not contain a fastening element, orient the specimen such that the fastening element side is facing up. Center the specimen across the gap, its length (direction 490, indicated on FIG. 5) should be parallel to the gap and its width (direction 491) should be perpendicular to the gap. Zero the load cell; start the tensile tester and the data acquisition.

Figure 7:
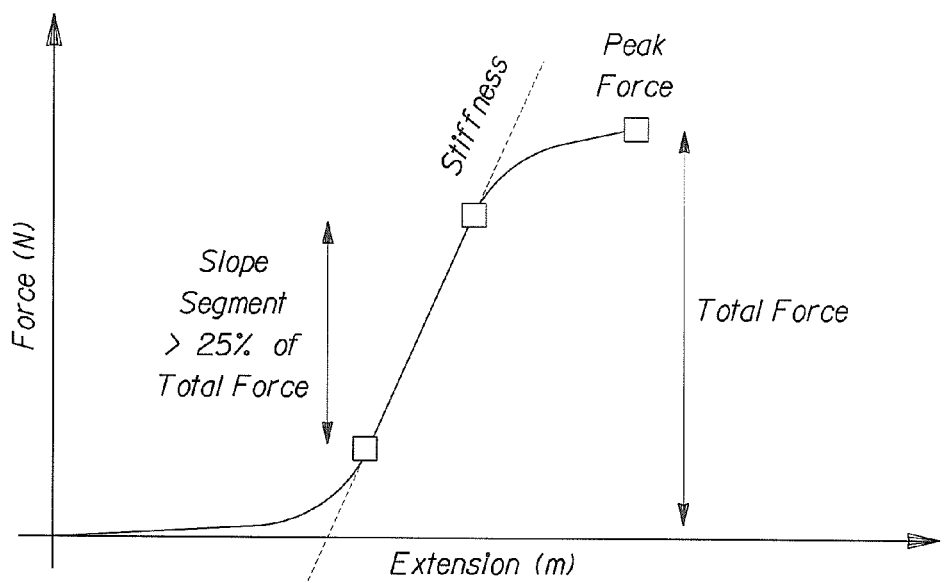
FIG. 7 is a graph showing Peak load and slope calculation areas on bending curve.

Program the software to calculate the maximum peak force (N) and stiffness (N/m) from the constructed force (N) verses extension (m) curve. Stiffness is calculated as the slope of the force/extension curve for the linear region of the curve (see FIG. 7), using a minimum line segment of at least 25% of the total peak force to calculate the slope. If the width of the element is not 13 mm, normalize the actual width to 13 mm as follows:

$$\text{Stiffness}_{(actual\ length)} = [\text{Stiffness}_{(13\ mm)}/13\ mm] \times \text{actual width (mm)}$$

$$\text{Peak Force}_{(actual\ length)} = [\text{Peak Force}_{(13\ mm)}/13\ mm] \times \text{actual width (mm)}$$

Report peak force to the nearest 0.1 N and the stiffness to the nearest 0.1 N/m.

Measurement of Exposure of Stiffening Elements

The exposed edges of the stiffening element are measured under a tension of 1.5 N/cm and 4.0 N/cm. The fastening member 100 (see FIG. 8) is carefully removed from the article either by cutting or using a freezing spray (such as Cytofreeze) to peel the intact member from the article. A total of five fastening members are tested and results are reported as an average of the replicates. All samples are preconditioned at about 23° C.±2° C. and about 50%±2% relative humidity for 24 hours prior to testing. Herein, width of the sample is defined as dimension 491 and length is defined as dimension 490 according to FIG. 8.

The test stand consists of a laboratory ring stand with an attached horizontal cross bar, two mechanical clamps, 1051 and 1061 to grip the sample, and hanging weights 1063 to apply the specified forces. Specifically the clamps are at least 5 mm wider than the length 122 of the fastening member and exert sufficient grip strength so that the sample does not slip in either clamp under the applied force. The upper clamp is mounted onto the cross bar and oriented such that the sample can be hung vertically without obstruction. The lower clamp allows the hanging of weights from the sample to provide the specified forces.

For the initial measurements under no tension, place the sample 100 on a flat surface with the fasteners 116 facing upward. Using a digital caliper, measure the length of the fastening member along its inner edge 302 and record to the nearest 0.1 mm as F1. Also measure the end region length 125 (FIG. 1B) at the interface 1700 and record to the nearest 0.1 mm as E1.

Measure the mass of the lower clamp and record to the nearest 0.01 g as C1. Calculate the mass of the hanging weights for each tension as follows:

$$W1\ (g) = [0.15\ N/mm \times F1\ (mm) \times 101.97\ g/N] - C1\ (g)$$

$$W2\ (g) = [0.40\ N/mm \times F1\ (mm) \times 101.97\ g/N] - W1\ (g)$$

Secure the first 10 mm of the inboard edge 102 of the specimen into the upper clamp. Secure the first 10 mm of the outboard end 104 of the specimen into the lower clamp. Allow the sample to hang vertically under the weight of the lower clamp. Add weight W1 to the lower clamp and within 30 seconds of application measure any exposed corners at each end of the stiffness member as follows (see FIG. 8):

Using a digital caliper, measure the linear distance parallel to 490, between where the first edge 1018 of the stiffness element and the leading edge 1010 of the panel region meet along the interface line 1700. Record this result to the nearest 0.1 mm as the exposed upper edge length U1. Next, measure the linear distance parallel to 490, between where the second edge 1017 of the stiffness element and the trailing edge 1012 of the panel region meet along the interface line 1700. Record this result to the nearest 0.1 mm as the exposed lower edge length L1.

With the sample still in place, add weight W2 to the lower clamp and within 30 seconds of application of the additional weight measure any exposed corners at each end of the stiffness member as described above. Record U2 as the upper exposed edge and L2 as the lower exposed edge, respectively.

Calculate the following Exposure Ratios (all lengths below in mm):

$$R1 = U1/F1 \times 100$$

$$R2 = U2/F1 \times 100$$

$$R3 = L1/F1 \times 100$$

$$R4 = L2/F1 \times 100$$

$$R5 = U1/E1 \times 100$$

$$R6 = U2/E1 \times 100$$

$$R7 = L1/E1 \times 100$$

$$R8 = L2/E1 \times 100$$

Measure five replicate fastening elements and report all Exposure Ratios as the average of the five replicates to the nearest 0.1%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a longitudinal axis;
   a lateral axis perpendicular to the longitudinal axis;
   a first waist edge on a first side of the lateral axis;
   a second waist edge on a second side of the lateral axis;
   a first longitudinal edge on a first side of the longitudinal axis;
   a second longitudinal edge on a second side of the longitudinal axis;
   a first leg elastic feature proximate to a portion of the first longitudinal edge;
   a second leg elastic feature proximate to a portion of the second longitudinal edge;
   a topsheet;
   a backsheet;
   an absorbent core positioned at least partially intermediate the topsheet and the backsheet;
   a first waist region on the first side of the lateral axis;
   a second waist region on the second side of the lateral axis;
   a first discrete fastening member joined to the absorbent article in the second waist region, the first discrete fastening member comprising:
      a first surface;
      a second surface;
      a first engaging component disposed on the first surface;
      a first receiving component comprising a nonwoven material disposed on the second surface;
      wherein the first engaging component overlaps at least a portion of the first receiving component in a z-direction;
      a first area on the first surface that is free of the first engaging component; and
      a first portion that is elastically extensible; and
   a second discrete fastening member joined to the absorbent article in the second waist region, the second discrete fastening member comprising:
      a first surface of the second discrete fastening member;
      a second surface of the second discrete fastening member;
      a second engaging component disposed on the first surface of the second discrete fastening member;
      a second receiving component comprising a nonwoven material disposed on the second surface of the second discrete fastening member;
      wherein the second engaging component overlaps at least a portion of the second receiving component in the z-direction;
      a second area on the first surface of the second discrete fastening member that is free of the first engaging component; and
      a second portion that is elastically extensible;
   wherein the first engaging component of the first discrete fastening member is configured to engage the second receiving component of the second discrete fastening member when the absorbent article is positioned on a wearer; or
   wherein the second engaging component of the second discrete fastening member is configured to engage the first receiving component of the first discrete fastening member when the absorbent article is positioned on the wearer.

2. The absorbent article of claim 1, wherein the first engaging component is smaller than the first receiving component, and wherein the second engaging component is smaller than the second receiving component.

3. The absorbent article of claim 1, wherein the first engaging component has a first width generally parallel with the lateral axis, wherein the second engaging component has a second width generally parallel with the lateral axis, and wherein the first width and the second width are substantially the same.

4. The absorbent article of claim 3, wherein the first receiving component has a first width generally parallel with the lateral axis, wherein the second receiving component has a second width generally parallel with the lateral axis, and wherein the first width and the second width are substantially the same.

5. The absorbent article of claim 1, wherein the first receiving component has a first width generally parallel with the lateral axis, wherein the first engaging component has a second width generally parallel with the lateral axis, and wherein the first width is larger than the second width.

6. The absorbent article of claim 1, wherein the second engaging component has a first width taken parallel with the lateral axis, wherein the second receiving component has a second width taken parallel with the lateral axis, and wherein the first width is larger than the second width.

7. An absorbent article comprising:
   a longitudinal axis;
   a lateral axis perpendicular to the longitudinal axis;
   a first waist edge on a first side of the lateral axis;
   a second waist edge on a second side of the lateral axis;
   a first longitudinal edge on a first side of the longitudinal axis;
   a second longitudinal edge on a second side of the longitudinal axis;
   a first leg elastic feature proximate to a portion of the first longitudinal edge;
   a second leg elastic feature proximate to a portion of the second longitudinal edge;
   a topsheet;
   a backsheet;
   an absorbent core positioned at least partially intermediate the topsheet and the backsheet;
   a first waist region on the first side of the lateral axis;
   a second waist region on the second side of the lateral axis;
   a first discrete fastening member joined to the absorbent article in the second waist region, the first discrete fastening member comprising:
      a first surface;
      a second surface;
      a first engaging component disposed on the first surface; and a first receiving component disposed on the second surface;

wherein the first engaging component overlaps at least a portion of the first receiving component in a z-direction; and a second discrete fastening member joined to the absorbent article in the second waist region, the second discrete fastening member comprising:

a first surface of the second discrete fastening member;

a second surface of the second discrete fastening member;

a second engaging component disposed on the first surface of the second discrete fastening member; and a second receiving component disposed on the second surface of the second discrete fastening member;

wherein the second engaging component overlaps at least a portion of the second receiving component in the z-direction;

wherein the first engaging component of the first discrete fastening member is configured to engage the second receiving component of the second discrete fastening member when the absorbent article is positioned on a wearer; or wherein the second engaging component of the second discrete fastening member is configured to engage the first receiving component of the first discrete fastening member when the absorbent article is positioned on the wearer.

8. The absorbent article of claim 7, wherein the first discrete fastening member comprises a nonwoven material.

9. The absorbent article of claim 8, wherein the second discrete fastening member comprises a nonwoven material, and wherein the topsheet comprises a nonwoven material.

10. The absorbent article of claim 7, wherein the absorbent core comprises an absorbent material comprising a superabsorbent material.

11. The absorbent article of claim 7, wherein the first discrete fastening member comprises a first area on the first surface that is free of the first engaging component, and wherein the second discrete fastening member comprises a second area on a first surface that is free of the second engaging component.

12. The absorbent article of claim 11, wherein the first discrete fastening member comprises a first portion that is elastically extensible.

13. The absorbent article of claim 12, wherein the second discrete fastening member comprises a second portion that is elastically extensible.

14. The absorbent article of claim 7, wherein the first engaging component is smaller than the first receiving component, and wherein the second engaging component is smaller than the second receiving component.

15. The absorbent article of claim 7, wherein the first engaging component has a first width generally parallel with the lateral axis, wherein the second engaging component has a second width generally parallel with the lateral axis, and wherein the first width and the second width are substantially the same.

16. The absorbent article of claim 7, wherein the first receiving component has a first width generally parallel with the lateral axis, wherein the second receiving component has a second width generally parallel with the lateral axis, and wherein the first width and the second width are substantially the same.

17. The absorbent article of claim 7, wherein the first receiving component has a first width generally parallel with the lateral axis, wherein the first engaging component has a second width generally parallel with the lateral axis, and wherein the first width is larger than the second width.

18. The absorbent article of claim 7, wherein the second engaging component has a first width taken parallel with the lateral axis, wherein the second receiving component has a second width taken parallel with the lateral axis, and wherein the first width is larger than the second width.

19. The absorbent article of claim 7, wherein the first engaging component is different from the first receiving component, and wherein the second engaging component is different from the second receiving component.

20. The absorbent article of claim 7, wherein the first discrete fastening member comprises a first material and a second, different material.

21. The absorbent article of claim 7, wherein the second discrete fastening member comprises a first material and a second, different material.

22. An absorbent article comprising:
a longitudinal axis;
a lateral axis perpendicular to the longitudinal axis;
a first waist edge on a first side of the lateral axis;
a second waist edge on a second side of the lateral axis;
a first longitudinal edge on a first side of the longitudinal axis;
a second longitudinal edge on a second side of the longitudinal axis;
a first leg elastic feature proximate to a portion of the first longitudinal edge;
a second leg elastic feature proximate to a portion of the second longitudinal edge;
a topsheet;
a backsheet;
an absorbent core positioned at least partially intermediate the topsheet and the backsheet;
a first waist region on the first side of the lateral axis;
a second waist region on the second side of the lateral axis;
a first discrete fastening member joined to the absorbent article in the second waist region, the first discrete fastening member comprising:
a first surface;
a second surface;
a first engaging component disposed on the first surface; and
a first receiving component disposed on the second surface;
wherein the first engaging component overlaps at least a portion of the first receiving component in a z-direction; and
a second discrete fastening member joined to the absorbent article in the second waist region, the second discrete fastening member comprising:
a first surface of the second discrete fastening member;
a second surface of the second discrete fastening member;
a second engaging component disposed on the first surface of the second discrete fastening member; and
a second receiving component disposed on the second surface of the second discrete fastening member;
wherein the second engaging component overlaps at least a portion of the second receiving component in the z-direction;
wherein the first engaging component of the first discrete fastening member engages with the second receiving component of the second discrete fastening member when the absorbent article is positioned on a wearer; or
wherein the second engaging component of the second discrete fastening member engages with the first receiving component of the first discrete fastening member when the absorbent article is positioned on the wearer.

23. The absorbent article of claim 22, comprising an elastically extensible waist member.

24. The absorbent article of claim 22, wherein the first discrete fastening member comprises a first area on the first surface that is free of the first engaging component, and wherein the second discrete fastening member comprises a second area on a first surface that is free of the second engaging component.

25. The absorbent article of claim 22, wherein the first engaging component is smaller than the first receiving component, and wherein the second engaging component is smaller than the second receiving component.

26. The absorbent article of claim 25, wherein the first receiving component has a first width generally parallel with the lateral axis, wherein the first engaging component has a second width generally parallel with the lateral axis, and wherein the first width is larger than the second width.

27. The absorbent article of claim 25, wherein the second engaging component has a first width taken parallel with the lateral axis, wherein the second receiving component has a second width taken parallel with the lateral axis, and wherein the first width is larger than the second width.

28. An absorbent article comprising:
a longitudinal axis;
a lateral axis perpendicular to the longitudinal axis;
a first waist edge on a first side of the lateral axis;
a second waist edge on a second side of the lateral axis;
a first longitudinal edge on a first side of the longitudinal axis;
a second longitudinal edge on a second side of the longitudinal axis;
a first leg elastic feature proximate to a portion of the first longitudinal edge;
a second leg elastic feature proximate to a portion of the second longitudinal edge;
a topsheet;
a backsheet;
an absorbent core positioned at least partially intermediate the topsheet and the backsheet;
a first waist region on the first side of the lateral axis;
a second waist region on the second side of the lateral axis;
a first discrete fastening member joined to the absorbent article in the second waist region, the first discrete fastening member comprising:
a first surface;
a second surface;
a first engaging component disposed on the first surface; and
a first receiving component disposed on the second surface;
wherein the first engaging component overlaps at least a portion of the first receiving component in a z-direction; and
a second discrete fastening member joined to the absorbent article in the second waist region, the second discrete fastening member comprising:
a first surface of the second discrete fastening member;
a second surface of the second discrete fastening member;
a second engaging component disposed on the first surface of the second discrete fastening member; and
a second receiving component disposed on the second surface of the second discrete fastening member;
wherein the second engaging component overlaps at least a portion of the second receiving component in the z-direction;
wherein the first engaging component of the first discrete fastening member at least partially overlaps with and engages the second receiving component of the second discrete fastening member when the absorbent article is positioned on a wearer; or
wherein the second engaging component of the second discrete fastening member at least partially overlaps and engages the first receiving component of the first discrete fastening member when the absorbent article is positioned on the wearer.

29. The absorbent article of claim 28, comprising an elastically extensible waist member.

30. The absorbent article of claim 28, wherein the first engaging component is smaller than the first receiving component, and wherein the second engaging component is smaller than the second receiving component.

* * * * *